US006953655B1

(12) United States Patent
Hassanein et al.

(10) Patent No.: US 6,953,655 B1
(45) Date of Patent: Oct. 11, 2005

(54) COMPOSITIONS, METHODS AND DEVICES FOR MAINTAINING AN ORGAN

(75) Inventors: Waleed H. Hassanein, Malden, MA (US); Shukri F. Khuri, Westwood, MA (US); Michael D. Crittenden, Hyde Park, MA (US); Vladimir Birjiniuk, Weston, MA (US)

(73) Assignee: The United States of America as represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 09/534,092

(22) Filed: Mar. 23, 2000

Related U.S. Application Data

(63) Continuation of application No. PCT/US98/19912, filed on Sep. 23, 1998, which is a continuation-in-part of application No. 09/054,698, filed on Apr. 3, 1998, now Pat. No. 6,046,046, which is a continuation-in-part of application No. 08/936,062, filed on Sep. 23, 1997, now Pat. No. 6,100,082.

(51) Int. Cl.[7] .............................. A01N 1/00; A01N 1/02
(52) U.S. Cl. ........................... 435/1.1; 435/1.2; 435/1.3
(58) Field of Search ........................... 435/1.1, 1.2, 1.3, 435/2

(56) References Cited

PUBLICATIONS

Merck Index, Eleventh Edition 1989, entry 4353.*
Turpin et al., "Effects of extracellular magnesium and beta adrenergic stimulation on contractile force and magnesium mobilization in the isolated rat heart", Magnesium Research 7:187–197 (1994).*

Dobrian et al., "In vitro formation of oxidatively–modified and reassembled human low–density lipoproteins Antioxidant effect of albumin", BBA 1169 :12–24 (1993).*

Birkett et al., "The fatty–acid content and drug binding characteristics of commercial albumin preparations", Clin. Chem. Acta 85 (3): 253–258 (1978).*

Watanabe et al., "Effects of free fatty acids on the binding of bovine and human serum albumin with steroid hormones", BBA 1289: 385–396 (1996).*

* cited by examiner

*Primary Examiner*—Sandra E. Saucier
(74) *Attorney, Agent, or Firm*—Hamilton, Brook, Smith & Reynolds, P.C.

(57) ABSTRACT

Compositions, methods, systems/devices and media are provided for maintaining a harvested organ in a functioning and viable state prior to implantation. The organ perfusion apparatus includes a preservation chamber for storing the organ during the preservation period. A perfusion circuit is provided having a first line for providing an oxygenated fluid to the organ, and a second line for carrying depleted fluid away from the organ. The perfusion apparatus also includes a device operably associated with the perfusion circuit for maintaining the organ at a substantially normothermic temperature.

17 Claims, 11 Drawing Sheets

COMPOSITIONS, METHODS AND DEVICES FOR MAINTAINING AN ORGAN

RELATED APPLICATION

This application is a Continuation of PCT/US98/19912, filed Sep. 23, 1998 (designating the U.S.) which is a Continuation-in-Part of U.S. Ser. No. 09/054,698 filed Apr. 3, 1998, now U.S. Pat. No. 6,046,046, which is a Continuation-in-Part of U.S. Ser. No. 08/936,062, filed Sep. 23, 1997, now U.S. Pat. No. 6,100,082, the entire teachings of which are incorporated herein by reference.

BACKGROUND OF THE INVENTION

1. Technical Field

The present invention relates to compositions, methods, systems/devices and media for maintaining a harvested (extracorporeal) animal organ in a functioning and viable state prior to transplantation or reimplantation. In particular, the present invention relates to compositions, methods, systems/devices and media for maintaining a harvested human or human-compatible organ in a functioning and viable state. The organ may also be assessed in such state or resuscitated after death.

The present invention also relates to an organ perfusion apparatus, and more particularly, to a perfusion apparatus and method and chemical compositions for extending the preservation period of an organ which has been harvested.

2. Discussion

While having many embodiments, the present invention is directed to systems, devices (apparatuses), methods and media for preserving organs in near ideal conditions and physiological states. This allows the organs to be stored for longer periods of time, reduces degradation of high energy phosphates during storage, reduces ischemia and reperfusion injury, and overall improves outcome. The increase in storage periods in a normal or near normal functioning state also provides certain advantages, for example, organs can be transported greater distances and there is an increased time for testing and evaluation of the organs.

It is estimated that one of every four patients listed for cardiac transplantation dies awaiting the availability of a suitable donated organ. While some progress has been made in making more donor organs available, the development of successful techniques for donor heart preservation has not kept pace with the demand for cardiac transplantation. With improvements in patient survival and the development of new immunosuppressive agents, heart transplantation has become more feasible, making the problem of organ supply even more critical. Despite the acceptable clinical results obtained with the current donor organ and donor heart preservation techniques, one of the major challenges that remains is the current inability to safely preserve the donor heart for more than four hours. Extending the preservation period beyond four hours using current preservation techniques significantly increases the risk of organ failure during or after transplantation; this failure correlates with the period and technique of storage. This four hour limitation also restricts the geographic area from which donor hearts can be transported for successful transplantation. Moreover, current methods of storing or preserving the heart or other organs make it impossible to fully or meaningfully test or evaluate the stored organ due to the storage of the organ in a non-functioning and/or hypothermic state.

Generally, current donor organ preservation protocols do not attempt to recreate an in vivo-like physiologic state for harvested organs. Instead, they utilize hypothermic (below 20° C. and typically at about 4° C.) arrest and storage in a chemical perfusate for maintaining the heart (non-beating) or other organ (non-functioning) for up to four hours. These protocols utilize a variety of crystalloid-based cardioplegic solutions that do not completely protect the donor heart from myocardial damage resulting from ischemia and reperfusion injuries. The most common cardioplegic preservation solutions used are The University of Wisconsin Solution (UW), St. Thomas Solution, and the Stanford University Solution (SU). In addition to myocardial damage, ischemia, reperfusion and/or increased potassium concentrations may also cause coronary vascular endothelial and smooth muscle injury leading to coronary vasomotor dysfunction, which is believed to be the leading cause of late organ failure. (Ischemia is generally defined as an insufficient blood supply to the heart muscle.)

Techniques have also been developed for perfusing the heart with the storage solution in the hypothermic state. Other organs (liver, kidney, lungs, etc.) have been maintained in a similar, non-functioning, hypothermic state. The heart or the other organs so preserved are then transported in this hypothermic state for only up to four hours until implantation.

As is well known in the art, for optimal donor heart or other organ preservation, the following principles apply and are thought to assist in the minimization of ischemic and/or reperfusion injuries: a) minimization of cell swelling and edema; b) prevention of intracellular acidosis; c) minimization of ischemia and/or reperfusion injury; and d) provision of substrate for regeneration of high-energy phosphate compounds and ATP during reperfusion. The current methods of hypothermic arrest and storage preservation have been shown to result in cell swelling, intracellular acidosis, and a degradation of high-energy phosphates. Moreover, studies in humans have clearly demonstrated significant endothelial dysfunction following donor heart preservation when utilizing hypothermic arrest and storage protocols. In some instances, an organ which has undergone hypothermic arrest is transplanted into the recipient and cannot be restarted or resuscitated after transplantation. In addition, many times inadequate preservation results in acute graft failure and the inability of the transplanted organ to resume normal function and sustain the recipient's circulation. The problem of acute graft failure then requires constant support of the recipient's circulatory system by ventricular assist devices and/or cardiopulmonary bypass until another donor heart can be located. In some instances, a suitable organ cannot be located in time which results in the death of the recipient. There is also increasing evidence from a number of recent clinical studies that the preservation of metabolic, contractile and vasomotor function is not optimized with current preservation protocols. See, e.g., Pearl et al., "Loss of Endothelium-Dependent Vasodilatation and Nitric Oxide Release After Myocardial Protection With University of Wisconsin Solution", Journal of Thoracic and *Cardiovascular Surgery*, Vol. 107, No. 1, January 1994.

Because the art has not been able to store harvested organs at near optimal endogenous conditions, and has not recognized such storage as feasible or desirable, it has attempted to use the above combination of hypothermic conditions and/or crystalloid-based cardioplegic solutions for protection against organ condition deterioration.

Another approach attempted in the art has been to simulate near normal physiologic conditions by harvesting almost all the donor's organs together. For example, Chien et al., "Canine Lung Transplantation After More Than Twenty-four Hours of Normothermic Preservation, *The Journal of Heart and Lund Transplantation*, Vol. 16, No. 3, March 1997, developed an autoperfusion set-up in which a swine heart was preserved in a beating, working state for up to 24 hours by being continuously perfused with non-compatible blood. While this system demonstrated the feasibility of safely extending the preservation time of the donor heart, this method is far too cumbersome and impractical for widespread use as it requires the removal and preservation of the lungs, liver, pancreas, and kidneys (en bloc) in combination with the heart, all in functioning condition, and all still interacting and interdependent.

There is a need in the art to achieve prolonged ex vivo or extracorporeal preservation of the donor heart or other organ that has been harvested from a donor by providing continuous sanguineous perfusion, while maintaining the donor heart or other organ in the normal (beating or functioning) state. Such a technique would eliminate the need to arrest the heart for storage in a hypothermic environment, reduce reperfusion injuries, and overcome many of the problems associated with hypothermic arrest and storage, many of which are clearly time dependent.

There is a further need in the art to provide an apparatus, method and physiologic media for creating an extracorporeal circuit for sanguineously perfusing the harvested organ at normothermic temperatures (about 20° C. to about 37° C.; preferably about 25° C. to about 37° C.) for prolonged preservation of the harvested organ for up to twenty-four hours or longer. Such an apparatus, method and media would optimally maintain the heart or other harvested organ in the beating or functioning state during the preservation period to insure pulsatile coronary flow and homogeneous distribution of the substrate. Such an apparatus, system, method and media would provide the ability to extend the preservation period of the harvested organ beyond the current four hour limit, while avoiding time dependent ischemic injury and prolonged ischemia, thereby preserving coronary endothelial vasomotor function, and preventing the metabolic degradation of high-energy phosphates.

Additionally, such an apparatus, method and media would allow for expanding the organ donor pool, increasing the histocompatibility matching time, and potentially reducing the incidents of cardiac allograft vasculopathy. It will be appreciated that prolonging the preservation period of the donor heart would have a dramatic impact on the practice of heart transplantation; a worldwide retrieval of organs would be made possible, thus increasing the pool of available organs. Organs would not go unused because of lack of suitable nearby recipients. Moreover, additional time in combination with storage in the functional state would allow evaluation and testing of the organ to determine, e.g., the immunologic and functional characteristics of each organ, thereby allowing a more complete assessment of the organ, reducing the risk of graft failure.

In summary, the prior art has failed to appreciate the feasibility and/or desirability of employing a near ideal physiologic state ex vivo for harvested organs.

This state is provided for by the compositions, methods and systems/devices of the present invention. A fluid or fluid media is provided comprising (1) donor-compatible whole blood (or leukocyte-depleted whole blood) and (2) a storage solution which includes a carbohydrate source, insulin and other hormones including epinephrin, electrolytes and a buffer such as a source of bicarbonate ions. This fluid or fluid media is delivered to at least one major vessel and optimally to the "exterior" portions of the organ substantially surrounding or bathing the organ. The compositions, methods, systems/devices and media of the present invention can thus be employed to provide ideal storage conditions at normothermic or substantially normothermic temperatures, allowing the organ to remain functioning.

SUMMARY OF THE INVENTION

The present invention provides a system for preserving a human or human-compatible harvested organ in need of preservation or resuscitation during a preservation or evaluation period prior to implantation, including transplantation or reimplantation. The system of the invention also allows the organ to be transported to alternate geographic locations during the preservation period. This system includes:

(a) containment means for containing said organ in communication with a physiologic media or fluid comprising (i) whole blood (or leukocyte-depleted whole blood) compatible with said organ and (ii) a preservation solution;

(b) delivery means for delivering said fluid to at least one major vessel of said organ;

(c) means for carrying said fluid away from said organ;

(d) temperature control means for maintaining the temperature of the perfusate and said organ at a normothermic temperature of about 20° C. to about 37° C.;

(e) pressure control means for controlling the pressure of said fluid;

(f) oxygenation means for oxygenating at least a part of said fluid;

(g) filtering means for removing unwanted filtrate from said fluid, said filtering means preferably positioned between said oxygenation means and said organ; and (h) flow control means for controlling the flow of at least a part of said fluid.

The system optionally includes means for delivering said fluid to said containment means so that the exterior of said organ is substantially completely bathed in or surrounded by said fluid.

The present invention also provides an organ preservation solution for the preservation of a human or human-compatible harvested organ in a functioning state at a normothermic temperature of about 20° C. to about 37° C. that is particularly useful in combination with the systems and methods of the present invention. These solutions include:

(1) a carbohydrate or other energy source;
(2) sodium chloride;
(3) potassium;
(4) calcium;
(5) magnesium;
(6) bicarbonate ion;
(7) epinephrin; and
(8) adenosine.

These solutions may further include a fatty acid as well as a pharmaceutical agent selected from nitroglycerin, ACE inhibitors, beta blockers, cytoprotective agents, antioxidants, antibiotics, antimicrobials, anti-fungal, antiviral, immunosuppressives, nonsteroidal anti-inflammatories, steroids, and mixtures thereof.

In a preferred embodiment, the organ preservation solution is substantially free of nonmetabilizable impermeants; and has a pH of about 7.4 to about 8.5.

The present invention also provides a method of preserving a human or human-compatible harvested organ in a functioning state during a preservation or evaluation period prior to transplantation or reimplantation. The method includes the steps of:

(a) providing an extracorporeal organ to be preserved or tested;
(b) providing a containment means for said organ;
(c) providing a preservation media or fluid; said fluid media comprising:
   (i) whole blood or leukocyte-depleted whole blood that is compatible with said organ; and
   (ii) a preservation solution comprising:
      (a) a metabolizable carbohydrate;
      (b) sodium chloride;
      (c) potassium;
      (d) calcium;
      (e) magnesium;
      (f) bicarbonate;
      (g) epinephrin; and
      (h) insulin;
(d) delivering the fluid to at least one major vessel of the contained functioning organ while the organ is maintained at a normothermic temperature of about 20° C. to about 37° C. In a preferred embodiment, the fluid is also delivered to the exterior of the organ.

The present invention provides systems, apparatuses, methods and media for providing optimal and prolonged ex vivo preservation of the donor organ or heart by implementing a method capable of continuous sanguineous perfusion in the normal or near-normal beating or functioning state. According to the systems, apparatuses, methods and media associated with the present invention, this preservation period can be extended for twenty-four hours or more with the heart or other organ maintained in a viable state.

Accordingly, by way of example, in one embodiment, a perfusion apparatus for maintaining a harvested organ during a preservation period is provided. The perfusion apparatus includes a preservation chamber for storing the organ during the preservation period. A perfusion circuit is provided having a first line for providing an oxygenated fluid to the organ, and a second line for carrying depleted fluid away from the organ. The perfusion apparatus also includes a device operably associated with the perfusion circuit for maintaining the organ at a substantially normothermic temperature. Moreover, the perfusion apparatus maintains the organ in a viable state.

In another embodiment, by way of example, a method of perfusing an organ or donor heart is provided. The method comprises providing a preservation chamber for containing the organ, and a perfusion circuit operably associated with the preservation chamber. The perfusion circuit includes a first line for delivering fluid to the organ and a second line for carrying fluid away from the organ. The method also includes providing several chemical solutions to the fluid in the perfusion circuit and perfusing the organ or donor heart with the fluid.

The compositions, methods, systems/devices and media of the present invention maintain the donor heart in the beating state during the preservation period to insure homogeneous distribution of the substrate. Maintaining the heart in the beating state further serves to sustain normal metabolic, contractile and endothelial vasomotor function beyond the four hour hypothermic arrest and storage period currently employed for donor heart preservation.

BRIEF DESCRIPTION OF THE DRAWINGS

The various advantages of the present invention will become apparent to one skilled in the art by reading the following specification and appended claims, and by referencing the following drawings in which:

DETAILED DESCRIPTION OF THE INVENTION

A description of preferred embodiments of the invention follows.

The present invention is directed to a perfusion apparatus and method for extending the preservation time of at least one human or human compatible organ, such as a human heart, which has been harvested for transplantation or reimplantation.

Figure 1:
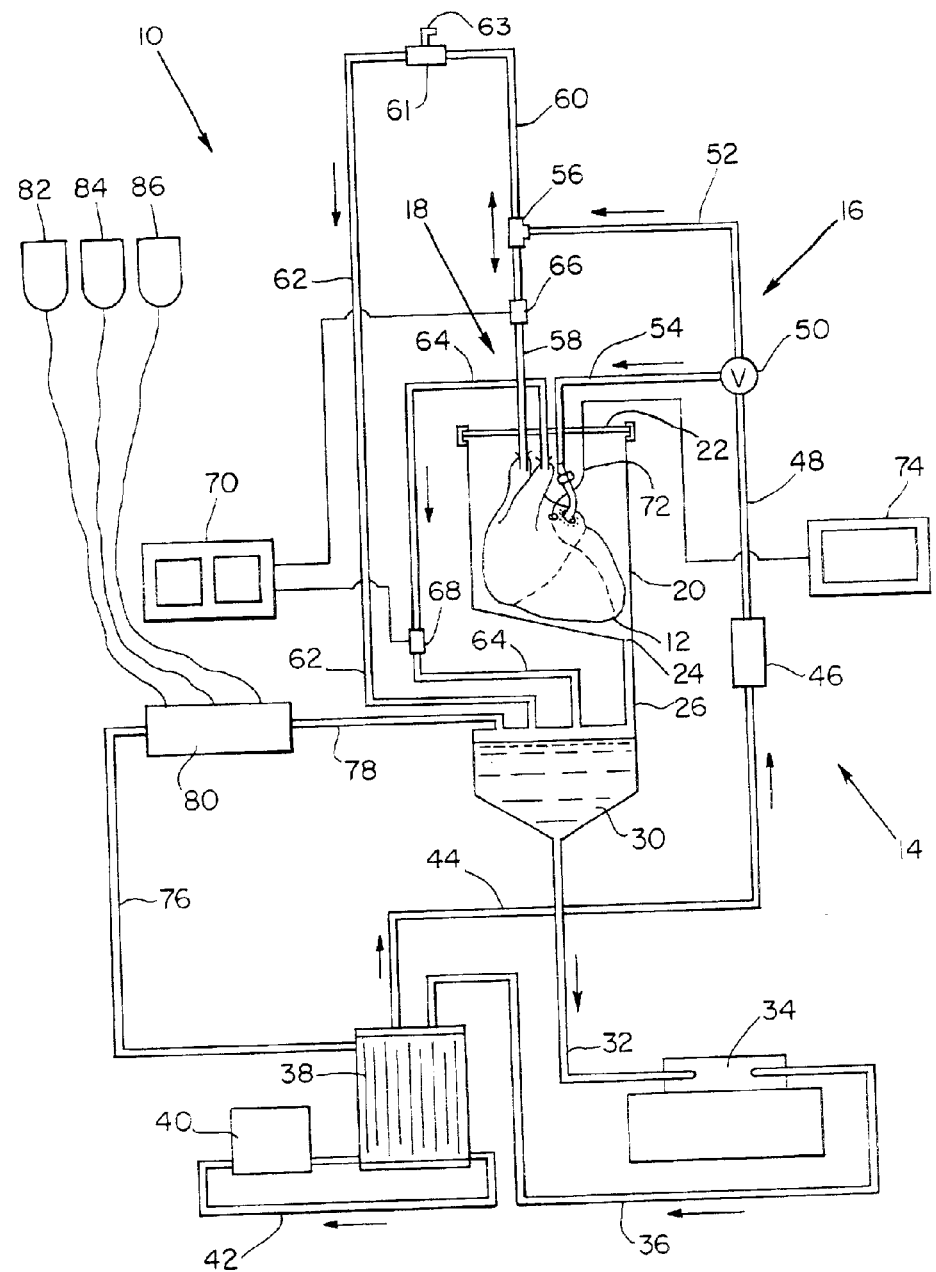
FIG. 1 is a schematic of the perfusion circuit and the components forming the perfusion system according to a preferred embodiment of the present invention.

Referring now to FIG. 1, the perfusion system 10 is shown in accordance with the present invention. While FIG. 1 illustrates a schematic of perfusion system 10, it ill be appreciated that various modifications to this schematic are within the scope of the present invention. The present invention allows the donor heart to be optionally harvested in the beating state and connected to perfusion system 10 where the organ is maintained in the beating state and provided with a pulsatile, physiologic coronary flow. Accordingly, the donor heart does not have to be arrested prior to its connection with perfusion system 10. Moreover, since the donor heart is not stored in the arrested hypothermic state during the preservation period, time dependent ischemic injury is eliminated. Another advantage of the present invention is that the perfusate used to extend the preservation period is comprised primarily of autologous (preferred) or in some cases homologous blood which is circulated through the perfusion system 10. Thus, the donor heart is provided with oxygen and essential nutrients during the preservation period which maintains the organ in a viable state. Moreover, cellular waste is carried away from the organ and filtered out of perfusion system 10.

Perfusion system 10 is designed to simulate the human cardiovascular system for maintaining the donor heart 12 in the beating state for periods up to or exceeding 24 hours. As with the human cardiovascular system, perfusion system 10 comprises a closed perfusion circuit 14 for circulating a fluid, comprised of autologous blood and other chemical compositions, to donor heart 12. Accordingly, perfusion circuit 14 includes one or more arterial lines 16 for providing oxygenated perfusion fluid to donor heart 12, and one or more venous lines 18 for carrying depleted perfusion fluid away from donor heart 12. As part of the method of the present invention, the arterial lines 16 are used for perfusing donor organ 12 in the both the non-working and working states. This method of antegrade perfusion will be discussed in more detail below.

With continued reference to FIG. 1, donor heart 12 is shown as being connected to perfusion circuit 14. The donor heart 12 is enclosed within a preservation chamber 20 which is preferably made of a hard, clear plastic to allow for visualization of the preserved organ. While it is preferred that preservation chamber 20 is formed from a plastic material such as LEXANO plastic, the preservation chamber 20 may also be made of a thick, yet soft flexible plastic in the form of a zipper bag (not shown) to accommodate the contour and shape of donor heart 12. When preservation chamber 20 is a hard plastic container, a plastic cover assembly 22 is used to seal the preservation chamber 20 and to maintain the sterility and humidity of donor organ 12. When a soft plastic preservation chamber (not shown) is employed, a zipper is used to seal the preservation chamber 20 and to protect the organ. A suitable drain 24 is provided at the lowest portion of preservation chamber 20. The drain 24 is connected to a reservoir 30 via drain line 26 to allow for the return of any blood escaping from the organ 12 during the instrumentation period, or from any leakage occurring during the preservation and transport period.

As disclosed, reservoir 30 is designed to contain approximately 500–3000 ml of fluid. Initially, reservoir 30 is primed with 500–2500 ml of autologous or cross-matched blood which is then pumped throughout perfusion circuit 14. Alternatively, compatible blood or blood substitute is within the scope of the present invention. The reservoir output line 32 is connected to the input of a centrifugal pump 34 (preferred) which circulates the perfusion fluid through the arterial lines 16 of perfusion circuit 14. The preferred pump for this application is the Biomedicus 550, manufactured by Medtronic, which propels the blood via magnetic field driven cones. While a conventional roller pump may also be used, the magnetic propulsion generated by centrifugal pump 34 is preferable to minimize hemolysis of the blood. If pulsatile flow is desired, a pulsatile pump such as the HEARTMATE® electric assist pump manufactured by Thermo-Cardiosystems Inc., or the NOVACOR left ventricular assist pump manufactured by Baxter Healthcare Corporation, may be employed. An exemplary pulsatile pump is that disclosed in U.S. Pat. No. 5,599,173 to Chen et al.

The centrifugal pump 34 propels the blood via pump output line 36 into a hollow fiber membrane oxygenator 38. The blood is oxygenated using a preferred mixture of 95% $O_2$ and 5% $CO_2$ at a rate of 1–2 L/min by membrane oxygenator 38. The preferred oxygenator is a hollow fiber membrane oxygenator, such as the Monolyth manufactured by Sorin Biomedical or the MINIMAX PLUS™ manufactured by Medtronic. While not specifically shown in FIG. 1, membrane oxygenator 38 is provided with the oxygen and carbon dioxide mixture through a regulated oxygen bottle 178. The oxygenator 38 also includes a plurality of ports (not shown) which allow pressurized perfusion fluid to be directed to other devices. A water heater/cooler 40 provides warmed water through a water circuit 42 which maintains the fluid within perfusion circuit 14 at about 37° C. (normothermia). The warmed perfusion fluid then maintains donor heart 12 at a normothermic temperature. Alternatively, water heater 40 can also remove heat from the water circulating through water circuit 42 for cooling the preservation fluid within perfusion circuit 14. Heat can be removed for a variety of reasons. For example, if the apparatus/ system 10 is preserving organ 12 in an excessively warm environment (i.e., exceeding normothermia), heat can be removed from the fluid to prevent the temperature from exceeding 37° C., or another predetermined temperature. Heat can also be removed from the fluid in order to cool the fluid below 37° C. which is desirable when inducing the preserved organ 12 into a low normothermic and/or mild hypothermic state. This is also desirable prior to arresting the organ 12. Enough heat may be removed for lowering the temperature of the fluid and organ down to about 20° C. The oxygenator output line 44 carries the oxygenated and rewarmed fluid to a filter 46. Preferably, the fluid is filtered with a leukocyte filter, such as the Pall leukocyte-depleting filter manufactured by Pall Filters.

The output of filter 46 is connected to a selector valve 50 via filter output line 48. Selector valve 50 may be placed in one of several positions for directing fluid flow to either the initial perfusion line 52 (for antegrade perfusion via the aorta), the left atrium supply line 54 (for antegrade perfusion via the left atrium), or both lines simultaneously (for priming purposes). Additionally, selector valve 50 may be turned off completely. As will be appreciated, lines 48, 54, and at times lines 52 and 58 form 10 the arterial side 16 of perfusion circuit 14. The opposite end of the initial perfusion line 52 is connected into a tee 56 which then branches to aorta line 58 and the afterload column, line 60. A straight connector 61 is used for connecting line 60 with the aorta return line 62. A Luer port 63 having a one-way anti-siphoning valve secured thereon is secured to connector 61 which acts as a one-way valve for allowing fluid pumped across connector 61 to flow through aorta return line 62 without siphoning additional fluid from afterload line 60. Luer port 63 operates by allowing air into aorta return line 62 for breaking the siphoning effect of the fluid. Accordingly, the peak of afterload column 60 is formed by connector 61 and Luer port 63.

The distal end of the afterload line 62 is attached to reservoir 30 to allow blood pumped through the aorta 130 to flow back to the reservoir 30. As will be discussed in more detail below, aorta line 58 provides bi-directional flow to and from donor heart 12, depending upon which mode the perfusion system 10 is operating. The height of afterload column 60 is adjustable between a range of vertical positions for selectively changing the afterload pressure against which the heart 12 will beat or pump. Once the fluid pumped through afterload column 60 crosses connector 61, it is returned to reservoir 30 via aorta return line 62. Additionally, a right ventricle return line 64 is connected to the pulmonary artery 132 to return coronary effluent to the reservoir 30. As will be appreciated, lines 58, 60, 62 and 64 form the venous side 18 or delivery means of perfusion circuit 14 when the heart is in the working state.

The aortic flow is measured by an ultrasonic flow probe 66 which is part of aorta line 58. Likewise, an ultrasonic flow probe 68 measures the coronary blood flow through right ventricle return line 64 of coronary effluent from the right ventricle to the reservoir 30. The aortic and coronary flow signals produced by ultrasonic flow probes 66 and 68 are recorded on a two-channel flow meter 70 which assists in monitoring the condition of the preserved organ 12, and the performance of perfusion system 10. The preferred flow meter 70 for use with the present invention is the two-channel flow meter manufactured by Transonic Systems.

The coronary flow is maintained within acceptable physiologic ranges (300–500 ml/min) by adjusting the height of the afterload column 60 above the heart 12 and adjusting the flow rate provided by pump 34. The afterload pressure is maintained at approximately 70 mm of mercury, but may be adjusted as necessary. A micro-tip pressure catheter 72 is inserted into the left ventricle via the left atrium 134 for measuring the intracavitary pressures of donor heart 12. A preferred pressure catheter 72 is of the type manufactured by Millar Instruments. All pressure measurements generated by pressure catheter 72 are recorded and displayed using a digital pressure recording system 74 which also assists in monitoring the condition of the preserved organ 12. As disclosed, pressure recording system 74 is capable of recording and displaying multiple pressure measurements.

One of the ports from oxygenator 38 is connected to a supply line 76 which provides oxygenated blood to a drip manifold 80. As disclosed, three IV bags 82, 84, 86 are connected to drip manifold 80 which provide various chemical compositions for the preserved organ (discussed in more detail below). Drip manifold 80 is known in the art and provides a mechanism for receiving a regulated drip rate of each chemical solution stored in the IV bags 82, 84, 86. As is known in the art, the drip rate can be regulated by an infusion pump (not shown). A manifold output line 78 carries the blood, enriched with the various chemical solutions to reservoir 30 for circulation to the donor heart 12.

A variety of materials may be used for creating the various lines and components of perfusion system 10. As almost all of the lines and components of perfusion circuit 14 are in constant contact with the blood perfusate, it is desirable to suppress the acute inflammatory response caused by exposure of the blood to extracorporeal artificial surfaces. To alleviate this problem, all of the contact surfaces within perfusion circuit 14 may be coated or bonded with heparin to reduce complement and granulocyte activation. As an alternative, heparin may be directly introduced into the fluid circulating through perfusion circuit 14, or other biocompatible surfaces may be utilized in circuit 14.

With continued reference to FIG. 1, the operation of perfusion system 10 will be described in more significant detail. As described above, the donor heart is harvested in either the beating state or the arrested state and placed into preservation chamber 20. At this point, centrifugal pump 34 is propelling oxygenated and rewarmed blood through line 48. During priming, selector valve 50 is placed into the position which allows blood to flow simultaneously through the initial perfusion line 52 and the left atrium supply line 54. Once the arterial lines 16 of perfusion circuit 14 are sufficiently primed to remove the presence of any air bubbles or air pockets, valve 50 is rotated into the position for supplying initial perfusion line 52 with fluid. Aortic line 58 can then be connected and secured to the aorta 130 using aortic cannula 120. This procedure allows blood to flow to the aortic line 58 for immediate perfusion of donor heart 12 via the aorta 130 in the non-working beating state. Optionally, afterload line 60 may be clamped for maximizing blood flow into the aorta 130. This procedure of antegrade perfusion via the aorta 130 is performed for approximately 10–15 minutes to allow for donor organ stabilization and to provide a period for instrumentation to be established. During this instrumentation period, the remaining flow lines are connected to donor heart 12. More specifically, the connection between aorta line 58 and the aorta 130 is completed, supply line 54 is connected to the left atrium 134, and the right ventricle return line 64 is connected to the pulmonary artery 132. The pulmonary veins, superior, and inferior vena cavae are then tied closed using #0 silk suture. During the initial connection protocol, any blood overflow is contained within preservation chamber 20 and returned to reservoir 30 via drain line 26.

At the end of the stabilization period, the flow to the aorta 130 is reduced by rotating selector valve 50 to the normal operating position which simultaneously and gradually increases the flow to the left atrium 134 via left atrium supply line 54 and gradually shuts off flow through initial perfusion line 52. Afterload line 60 is also unclamped. This procedure then switches the donor heart 12 from the non-working state into the working state, in which blood is pumped through the venous lines 18 of perfusion circuit 14 by the donor heart 12. It should be specifically noted that donor heart 12 remains beating at all times. Blood flow to donor heart 12 through arterial lines 16 is assisted by centrifugal pump 34. The donor heart 12 is allowed to beat against an afterload pressure created by the vertical position of afterload column 60 above the preservation chamber 20 thereby generating a pulsatile coronary flow. Additionally, oxygenated blood is provided to the coronary vascular system, and de-oxygenated blood from the coronary vascular system is pumped from the right ventricle into the pulmonary artery return line 64 and returned to reservoir 30. At this point, donor heart 12 can be maintained in the viable beating state for the duration of the preservation period. While the perfusion system 10 has been specifically described for preserving a heart, the apparatus and method associated with the present invention is particularly well suited for extending the preservation time for any solid organ by eliminating lines 52, 58, 60 and 62, and using line 54 to cannulate the organ's artery, and line 64 to cannulate the vein of the preserved organ. Accordingly, organs including the kidney, liver, lung, pancreas, and small intestine can be preserved for extended periods of time by perfusion system 10.

Figure 2:
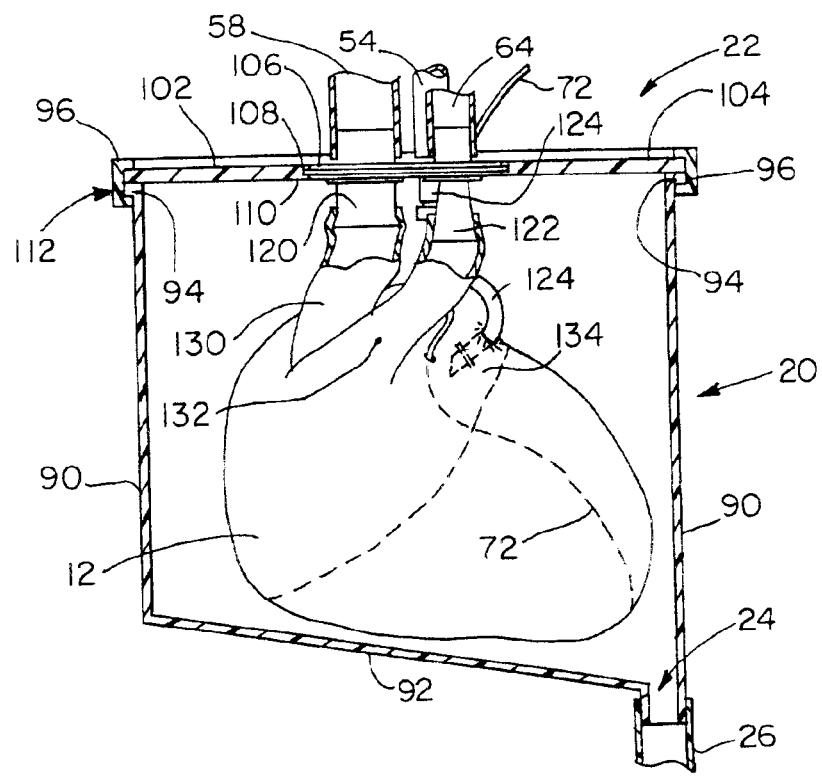
FIG. 2 is a cross-sectional view of the preservation chamber for maintaining the donor heart in the beating state according to a preferred embodiment of the present invention.

Turning now to FIG. 2, the preservation chamber 20 and the connections between the various cannula and the donor heart 12 are shown in more detail. As disclosed, preservation chamber 20 has an open top, and is defined by a generally cylindrical side wall 90 and a sloped bottom 92 which promotes the flow of fluid into drain 24 for return to reservoir 30 via line 26. Sloped bottom 92 further accommodates the donor organ 12 in a more correct anatomical position during the instrumentation and preservation periods. The top of cylindrical side wall 90 includes an outwardly protruding flange 94 around its circumference for providing an additional surface for receiving the cover assembly 22.

Figure 3:
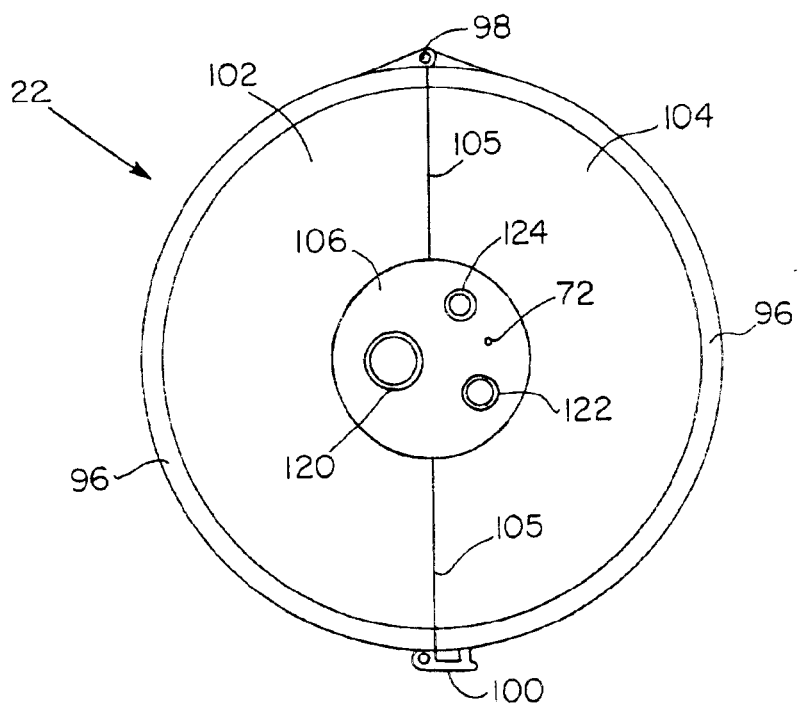
FIG. 3 is a top plan view of the cover assembly utilized with the preservation chamber according to the present invention.

Referring now to FIGS. 2 and 3, the components of cover assembly 22 are described in more detail. The outer circumference of cover assembly 22 is defined by a clamping ring 96 including two halves which are connected by a hinge 98. The two halves of clamping ring 96 can be realizably secured via snap lock 100. The remaining portion of the cover assembly 22 is formed by first cover 102 and second cover 104 which together form a circular cover plate having an aperture in the center thereof for receiving cannula plate 106. Clamping ring 96 has a generally U-shaped cross-section which is designed for receiving flange 94 and first and second covers 102, 104 for creating a tight seal as shown in FIG. 2. The abutting edges 105 between first cover 102 and second cover 104 include a tongue-and-groove structure (not shown) for providing additional rigidity and sealing capability to cover assembly 22. In a similar fashion, cannula plate 106 includes an annular tongue 108 which fits within an annular groove 110 formed within first cover 102 and second cover 104 for securing cannula plate 106 within cover assembly 22. While the tongue-and-groove arrangement associated with abutting edges 105 is not specifically shown, one skilled in the art will readily appreciate that this arrangement is substantially similar to the arrangement of annular tongue 108 and annular groove 110.

While several variations exist for arranging cover assembly 22, it is preferred that first cover 102 and second cover 104 are permanently secured to there respective side of clamping ring 96. In this fashion, an annular channel 112 remains along the lower inside circumference of clamping ring 96 for receiving flange 94 when the cover assembly 22 is placed on top of preservation chamber 20. Upon properly engaging annular channel 112 with flange 94, both halves of clamping ring 96 can be brought together for securely fastening snap lock 100 so that the cover assembly 22 may properly maintain the sterility and humidity of the enclosed organ.

Another advantage provided by cover assembly 22 is that cannula plate 106 is a separate component which interlocks with first and second covers 102, 104 of cover assembly 22 upon installation and securement thereof. As such, the various cannulae secured within cannula plate 106 can be attached to the appropriate locations on the organ 12 prior to installing cover assembly 22. The cannula plate 106 also positions each cannula in the proper location while the organ 12 is connected to perfusion system 10. More specifically, cannula plate 106 includes a first aperture for receiving the aortic cannula 120, a second aperture for receiving the arterial cannula 122, a third aperture for receiving the left atrial cannula 124, and a fourth aperture for receiving the pressure catheter 72. Each individual cannula is snapped into cannula plate 106 to provide a secure connection. It is further contemplated that each cannula has a standard sized top tube for snapping into the cannula plate 106, and a variably sized flared lower tube for fitting within its associated artery or vein. Therefor, if a cannula with a smaller or larger lower tube is required, it can be swapped into cannula plate 106 without removing the other cannulae. Accordingly, the design of cannula plate 106 provides a modular component which easily and securely integrates with cover assembly 22.

In operation, the fully assembled cannula plate 106 is held in proximity to the beating organ 12 so that aorta 130 can be connected to aortic cannula 120, the pulmonary artery 132 can be connected to the arterial cannula 122, and the left atrial cannula 124 can be properly inserted and secured within the left atrium 134. Preferably, a surgical grade cable tie (not shown) is used to secure the aorta 130 around the aortic cannula 120, and the pulmonary artery 132 around the arterial cannula 122. The left atrial cannula 124 is secured within the left atrium 134 using size 2-0 prolene surgical suture. As disclosed, the surgical grade cable ties provide a leak-proof seal, and a larger surface area for securing the arteries around there cannula without risk of tearing the tissue. This in turn assists in properly supporting donor heart 12 within preservation chamber 20. In some instances, as with a smaller donor heart 12, the heart may be suspended by the aorta 130 within preservation chamber 20.

After properly securing the organ to the components of cannula plate 106 within preservation chamber 20, each half of lid assembly 22 can be fitted around the outside circumference of cannula plate 106 so that the cover assembly 22 may be secured on top of the preservation chamber 20. The cover assembly 22 and cannula plate 106 then serve to suspend donor heart 12 within the preservation chamber 20. As best shown in FIG. 2, the pulmonary artery line 64 is secured to the arterial cannula 122, the aorta line 58 is connected to the aortic cannula 120, and the left atrium supply line 54 is connected to the left atrial cannula 124. Once all connections have been properly made (approximately 15 minutes), the organ is allowed to beat for approximately 10–15 minutes in the non-working state as described above for stabilization. After the stabilization and instrumentation period, the donor heart is then allowed to beat in the working state against the afterload created by afterload column 60. The preserved organ may continue to beat in the working state for the duration of the preservation period; up to or exceeding 24 hours.

According to the studies performed using perfusion system 10 to support animal hearts, the apparatus and method of the present invention allow the preserved organ to be maintained in the beating state for up to 24 hours or longer with minimal to no myocardial damage. As part of pilot studies using animal hearts, blood electrolytes of donor hearts maintained in the beating state were measured at one hour, six hour and twelve hour intervals. Analysis of the blood electrolytes indicated that the levels of glucose, sodium (Na), chlorine (Cl), potassium (K), calcium (Ca) and bicarbonate HCO3 remained substantially at baseline levels throughout the preservation period. Accordingly, the apparatus and method of the present invention allow a donor heart to be maintained in the viable beating state for periods beyond the current four hour limitation associated with current hypothermic arrest and storage techniques.

Also associated with the apparatus and method of the present invention are three separate chemical solutions operative in the preservation of the organ 12. As disclosed, the three chemical solutions replenish the preserved organ with energy as it is consumed by the cellular activity, maintain the blood electrolytes at physiologic levels, and stimulate the cardiac conduction system for maintaining the donor heart in the beating state during the preservation period. The three chemical solutions are provided to reservoir 30 through drip manifold 80 as previously discussed, which assists in regulating the proper drip rate for each chemical solution. The first solution is stored within IV bag 82, the second solution is stored within IV bag 84, and the third solution is stored within IV bag 86.

Prior to perfusing the organ 12, the perfusion system 10 is primed with 100–250 ml of the primary solution (stored in IV bag 82), 12.5–25 mg of Mannitol (a complex sugar) or a suitable substitute, and preferably 125–250 mg of methylprednisolone sodium succinate or a suitable substitute. The Mannitol acts as an impermeant to increase the osmotic pressure of the perfusate, which serves to minimize or reduce edema formation in the preserved organ. Mannitol also acts as an oxygen or free radical scavenger to attenuate the perturbations of reperfusion injury and extracorporeal perfusion to the preserved organ. Moreover, the Mannitol is especially useful when the perfusate contact surfaces of perfusion circuit 14 are non-heparin bonded. However, Mannitol can still be used within perfusion circuit 14 even when all of its components have heparin bonded surfaces, so that the benefits provided by Mannitol can be fully utilized. The methylprednisolone sodium succinate is a steroid which acts as a cell membrane stabilizer for avoiding cell lysing during reperfusion and also acts as an immunosuppressive agent.

As disclosed, the first solution, or primary solution is a solution comprising sugar and various electrolytes. The first solution is formulated by combining several chemical components with preferably one liter of dextrose, 5% (with a preferred range of between 2.5% and 5% dextrose) in normal saline (0.9 molar sodium chloride). Alternatively, the dextrose may be delivered in half normal saline (0.45 molar sodium chloride). Dextrose is one of the major components needed by the preserved organ for cellular energy and ATP production. The dextrose, a form of glucose, acts by stimulating the aerobic pathway of glycolysis and the Krebs' cycle; the primary biochemical processes for energy production in the body. To this dextrose solution is added, 4 milliequivalents of potassium chloride (with a preferred range of between 4 meq and 6 meq). The purpose of the potassium chloride is to maintain normal physiologic levels of intra and extra-cellular potassium, thus abolishing arrhythmias (abnormal heart rhythm). Preferably, 35 units of regular insulin (with a preferred range between 20 units and 40 units) are also added to the primary solution. Insulin acts to drive glucose into the cells to make it readily available for the cytoplasmic and mitochondrial metabolic processes. Insulin also drives extracellular potassium into the cells helping in achieving a physiologic potassium level. Preferably, 1.5 grams of calcium chloride (with a preferred range of between 1.0 grams and 1.5 grams of calcium chloride) are also added. Calcium chloride is the primary cation required for myocardial muscle contraction, and its presence in normal physiologic levels is important for maintaining the donor heart in the beating or working state. The calcium chloride also acts as a positive inotrope for increasing the force of myocardial contractility, again required for normal myocardial function during preservation of the donor heart in the beating state. The primary drip solution stored in IV bag 82 is provided to drip manifold 80 at a preferred drip rate of 15 ml/hr (with a preferred range of between 15 ml/hr and 40 ml/hr). In an alternate embodiment of the primary solution, preferably 5 ml of sodium bicarbonate (with a preferred range of between 5 ml and 10 ml) is added to the solution bag to maintain a normal pH of between 7.4–7.5. Thus, the addition of sodium bicarbonate acts to buffer the solution.

The second solution disclosed is preferably a fatty acid solution, i.e., saturated and/or unsaturated monocarboxylic acids in solution. Both short chain and long chain fatty acids may be used including C3 to C10, C3 to C8 and preferably, C3, C7 or C8 chain fatty acids. In the preferred embodiment, this is achieved with a 20% intralipid solution (with a preferred range of between 10% and 20% being employed). The preferred concentrations of the intralipid solution are currently available from commercial manufacturers as a 10% intralipid solution or a 20% intralipid solution. Alternatively, soyacal may also be used which provides fatty acid and is derived from a soybean base. The intralipid solution is provided to drip manifold 80 at a preferred rate of 2 ml/hr (with a preferred range of between 1 ml/hr and 2 ml/hr). The intralipid solution is preferred for use with the present invention due to its high content of fatty acids, which can be directly metabolized by the cells of the donor heart. The fatty acids are the primary source of energy for the myocardial cell. The second source of energy for the myocardial cell is the glucose provided by the first drip solution.

The third solution disclosed is created by mixing preferably 250 ml of normal saline (with a preferred range of between 250 ml and 500 ml) with preferably 4 mg of epinephrine (with a preferred range of between 4 mg and 8 mg of epinephrine). This solution is used to provide the donor heart with base-line levels of catecholamines necessary for normal heart rate and contractility, Epinephrin is also used to maintain the heart rate within a normal physiologic range. Epinephrin works by stimulating the receptors of the sympathetic nervous system in the preserved heart. Studies made in conjunction with the present invention have demonstrated a marked depletion of plasma catecholamines levels after 2–6 hours of preservation in the perfusion system 10, through multiple measurements of serum catecholamine levels. The third solution is provided to drip manifold 80 at a preferred drip rate of 4 ml/hr (with a preferred range of between 2 ml/hr and 12 ml/hr) for maintaining base-line levels of catecholamines. In an alternate embodiment of the third solution or epinephrine solution, preferably 2 ml of sodium bicarbonate (with a preferred range of between 2 ml and 5 ml) is added to the solution bag to maintain a normal pH of between 7.4–7.5. Thus, the addition of sodium bicarbonate acts to buffer the solution.

Because the preserved organ 12 is maintained in the beating state, it is important that the heart be provided with oxygenated blood at the normothermic temperature. The preserved organ should also be provided with a balanced substrate consisting of the three disclosed chemical solutions. Additionally, since the preservation period is up to 24 hours or longer, the preserved organ 12 should be provided with significant amounts of energy and replenished with various chemical compounds for maintaining the normal beating operation. As part of the alternative preferred embodiment, the fatty acids can be delivered into the fluid media via solution bag 274, and the remaining chemical compositions can be delivered into the fluid media via solution bag 272.

Figure 4:
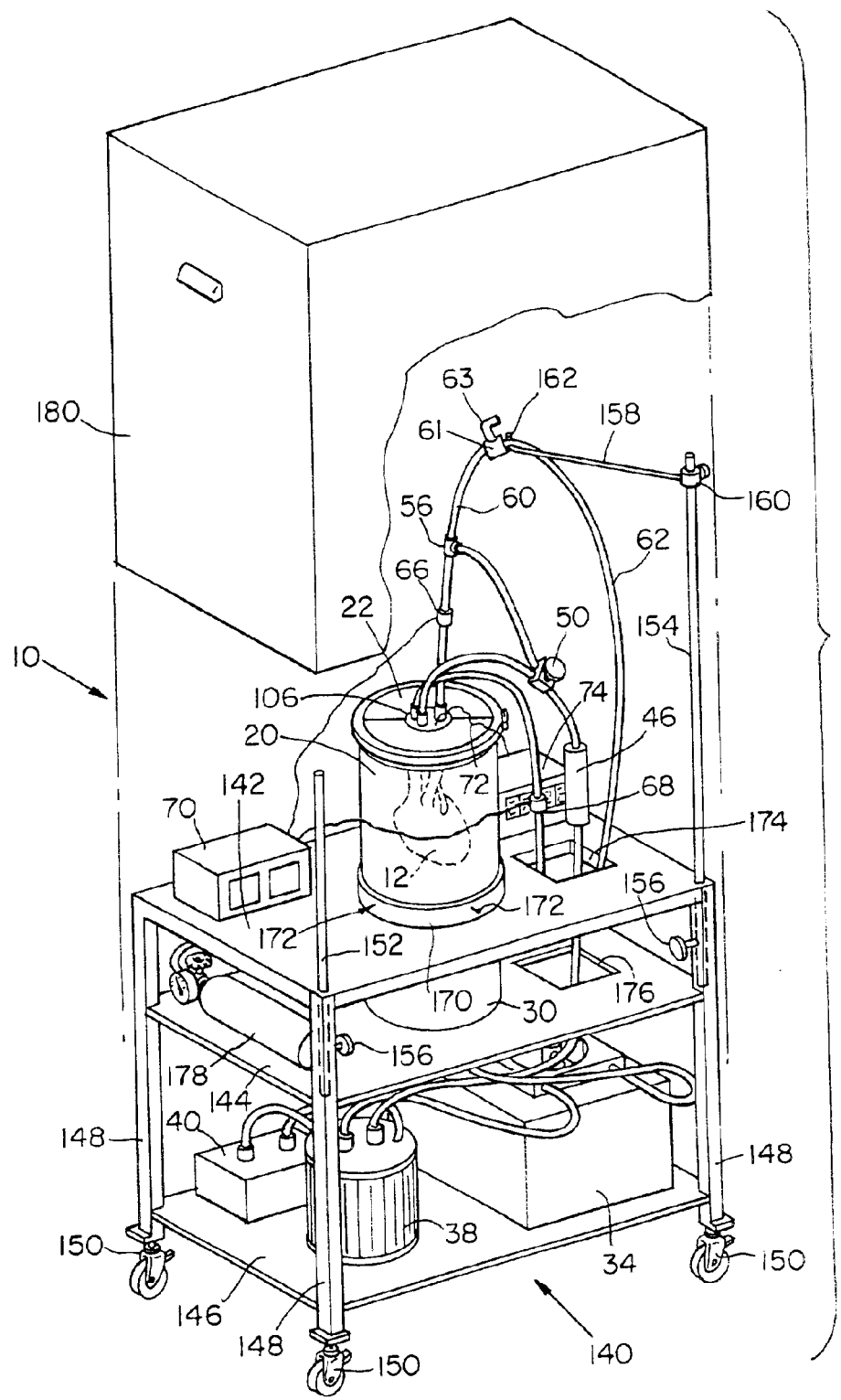
FIG. 4 is a perspective view of the perfusion system installed on a mobile cart for facilitating transportation of the harvested organ, also according to a preferred embodiment of the present invention.

Turning now to FIG. 4, perfusion system 10 is shown as being installed on a mobile cart 140. As disclosed, cart 140 includes a top shelf 142, a middle shelf 144, and a lower shelf 146 which are supported by four posts 148. The lower end of each post 148 includes a locking caster 150. Associated with two of the posts 148 are a pair of adjustable poles 152, 154. The height of each pole 152, 154 can be adjusted using a threaded locking knob 156. Pole 154 includes an adjustable arm 158 which is primarily intended for supporting lines 60 and 62 for setting the height of the afterload column 60. Adjustable arm 158 also includes a threaded locking knob 160 for setting the height of the adjustable arm 158 and a hook portion 162 at the outboard end thereof for supporting lines 60, 62.

The top shelf 142 of cart 140 includes a circular aperture and annular clamp 170 for receiving and securing preservation chamber 20. As disclosed, preservation chamber 20 is placed into annular clamp 170 and secured with a plurality of thumb screws 172. While not specifically shown, annular clamp 170 and thumb screws 172 may be replaced with a circular clamp operated by a release lever for securing preservation chamber 20. Top shelf 142 is also provided with a square aperture 174 which allows the various lines to pass from the preservation chamber 20 down to the components below. Middle shelf 144 also includes a square aperture 176 which provides a similar function. As disclosed, reservoir 30 is positioned directly below preservation chamber 20 on the middle shelf 144. Middle shelf 144 also includes an oxygen bottle and regulator 178 for providing the requisite oxygen and carbon dioxide mixture to membrane oxygenator 38. The bottom shelf 146 is particularly well suited for supporting the centrifugal pump 34, membrane oxygenator 38, and water heater 40. Since these are typically the heaviest components associated with perfusion system 10, the location of these components on bottom shelf 146 serves to lower the overall center of gravity which further stabilizes mobile cart 140. Top shelf 142 provides ample surface area for supporting the flow meter 70 and the digital pressure recording system 74. However, additional electronic monitoring and feedback devices could also be supported by top shelf 142 for use with perfusion system 10. Finally, a clear hard plastic cover 180 can be fitted on top of cart 140. Cover 180 allows visual inspection of the components stationed on top shelf 142, while also providing additional protection to the perfusion system 10 and preservation chamber 20.

As will be appreciated by one skilled in the art, mobile cart 140 provides significant enhancement to the overall function of perfusion system 10. More specifically, perfusion system 10 may be wheeled into the operating room from a separate storage location. Additionally, the cart 140 may be easily moved within the operating room or rooms during both organ harvesting and organ implantation.

Moreover, the locking casters 150 allow cart 140 to be fixed in one location to prevent unwanted movement. The overall size of mobile cart 140 is such that it can be easily transported in both land based vehicles, such as an ambulance, or within private or commercial aircraft, such as a hospital helicopter or airplane. Accordingly, mobile cart 140 serves to increase the overall efficiency of transporting a harvested organ for implantation into the recipient.

Figure 5:
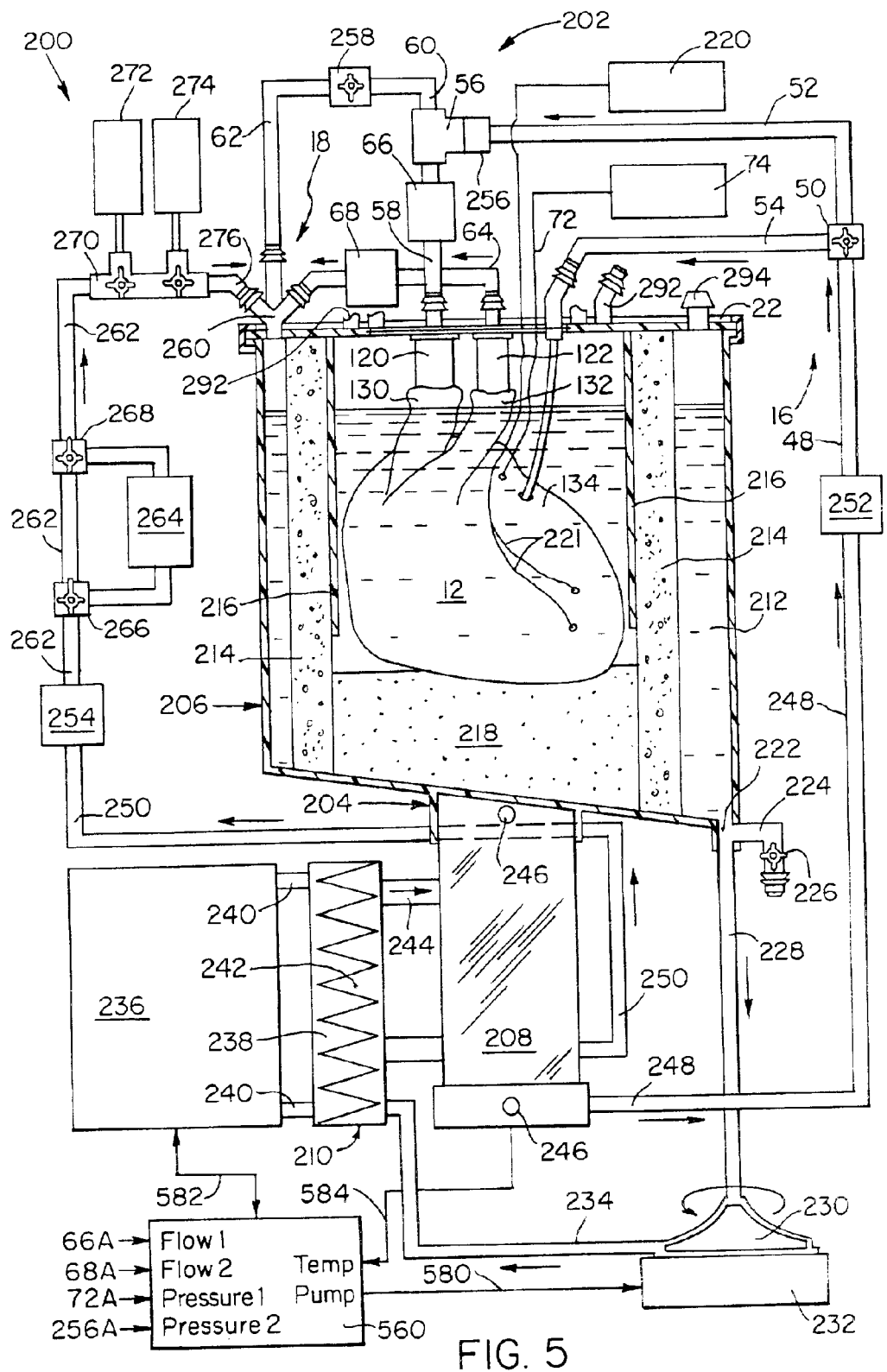
FIG. 5 is a schematic diagram of the preservation circuit utilizing an integrated container and reservoir according to a preferred embodiment of the present invention.

Turning now to FIG. 5, the preservation system 200 of the present invention is shown in accordance with another preferred embodiment. It should be noted that preservation system 200 shares many similar components, and operates in a similar fashion as perfusion system 10 disclosed above. Thus, preservation system 200 also serves to reduce or eliminate time dependent ischemia associated with the prior techniques, minimize or eliminate edema, and deliver chemical enhancements to the preserved organ in a physiologic fashion. However, several improvements are discussed in association with preservation system 200 which will be described in more detail below. The present configuration of preservation system 200 also allows the donor heart 12 to be harvested in either the beating state or non-beating (arrested) state, and connected to preservation system 200 where the organ is maintained in the beating state and provided with a physiologic coronary flow of the preservation fluid.

As specifically shown in FIG. 5, the physiologic coronary flow is provided in a pulsatile fashion because the heart is beating in the working state for generating its own pulsatile flow. As discussed above, a particular advantage of the present invention is that the fluid media used to extend the preservation period is comprised primarily of autologous, homologous, or compatible blood which is circulated through preservation system 200. The chemical enhancements described herein are then combined with the blood for creating the preservation fluid media. Thus, the donor heart 12 is provided with oxygen and various chemical enhancements during the preservation and maintenance period for maintaining the organ in a viable state. For purposes of the present invention, viable state means a state in which the organ is functioning at any physiological level. Moreover, cellular waste and metabolites are carried away from the organ in a normal physiologic fashion and filtered out of preservation system 200. Alternatively, the cellular waste and metabolites can be diluted or reduced from within preservation system 200 by transfusing the blood within the reservoir. Additional cellular waste and metabolites can be removed with a suitable hemodialysis filter.

Preservation system 200 is designed to simulate the in-vivo human cardiovascular system for maintaining the donor heart 12 in the beating state for periods up to or exceeding twenty-four (24) hours. The preservation technique can be operated at a normothermic temperature of about 37° C., or at a substantially normothermic temperature of about 20° C. to about 37° C. As disclosed above, preservation system 200 comprises a closed preservation circuit 202 for circulating a fluid media, comprised of autologous blood, or alternatively homologous or compatible blood or blood substitute, and other chemical compositions comprising a preservation solution, to donor heart 12. As disclosed, the blood may be either whole blood or leukocyte depleted whole blood which is compatible with the organ. As shown, preservation circuit 202 includes one or more arterial lines 16 for providing oxygenated fluid to donor heart 12, and one or more venous lines 18 for carrying depleted fluid away from donor heart 12. According to this embodiment, the arterial lines 16 comprise the delivery means for delivering the fluid media to at least one major vessel of the organ, and the venous lines 18 comprise the means for carrying the fluid media away from the organ. As part of the method of the present invention, the arterial lines 16 are used for supplying fluid and/or perfusing donor organ 12 in either the non-working and working states.

With continued reference to FIG. 5, donor heart 12 is shown as being connected to preservation circuit 202. The donor heart 12 is enclosed within containment means 206 for containing the donor heart in communication with the fluid media. As disclosed, the containment means 206 is a hard plastic chamber for protecting and allowing visualization of the preserved organ. It is preferable that the containment means or preservation container 206 is made from clear polycarbonate, or other suitable hard plastic material. As disclosed, the containment means 206 may also comprise a thick, yet soft flexible plastic container in the form of a bag having a single or double zip-lock closure. Preferably, the bag is formed to accommodate the contour and shape of the preserved organ, such as donor heart 12, or any other solid organ.

As shown, preservation container 206 forms part of an integrated preservation device 204 which also includes a hollow fiber membrane oxygenator 208 and a heat exchanger 210. As part of this embodiment, oxygenator 208 comprises the oxygenation means for oxygenating at least part of the fluid media, and heat exchanger 210 along with it's associated water heater/cooler unit 236 for providing temperature controlled water comprises the temperature control means for maintaining the temperature of the organ at a temperature of about 20° C. to about 37° C. As will be appreciated, preservation container 206 is substantially similar to preservation chamber 20 disclosed above. However, as part of the present invention, preservation container 206 is slightly larger for simultaneously defining a fluid reservoir 212 for storing a supply of the preservation fluid or fluid media. As shown, it is preferable that preservation container 206 be large enough for defining a fluid reservoir 212 for containing approximately 500–3000 ml of fluid. This design feature allows donor heart 12 to be substantially immersed and/or bathed within the fluid within preservation container 206, if desired.

Preservation container 206 has an open top, and is defined by a generally cylindrical side wall 90, and having a sloped bottom 92 which promotes the flow of fluid into reservoir outlet 222. The top of cylindrical side wall 90 also includes an outwardly protruding flange 94 around its circumference for providing an additional surface for receiving the cover assembly 22 shown in FIG. 2. The remaining portions of cover assembly 22 are substantially similar to that disclosed above except for the addition of multiple blood inlets or ports 292 and one or more safety valves 294. Preservation container 206 also includes a pair of filters 214 which serve to remove particulate matter from the preservation fluid. Each filter 214 preferably comprises a polyurethane sponge. Accordingly, filters 214 comprise at least a portion of the filtering means for removing unwanted filtrate from the fluid media. One side of each filter 214 includes a silicone defoaming screen 216 which further assists in reducing and/or removing bubbles and foam from the recirculating preservation fluid. A silicone foam pad 218 is positioned within the lower portion of preservation container 206 for supporting donor heart 12 during the preservation period. The silicone pad 218 also acts as a sponge for shock absorption. As shown, an additional port 224 having a stopcock 226 is also provided for instances in which it is desirable to drain the preservation fluid within fluid reservoir 212 while the preservation circuit 202 is being operated. Such an instance might include transfusing the blood contained in reservoir 202 for removing unwanted metabolites.

An outlet line 228 is provided for connecting reservoir outlet 222 with a centrifugal pump head 230. A pump head driver 232 is provided for generating the rotational force and control which is provided to pump head 230. The preferred pump head and pump for this application is the Biomedicus 550, manufactured by Medtronic, Inc. which propels the blood via magnetic field driven cones and includes a biocompatible surface, which minimizes hemolysis of the blood. As will be appreciated, centrifugal pump head 230 and driver 232 comprises both the pressure control means for controlling the pressure of the fluid media, and the flow control means for controlling the flow of at least part of the fluid media.

The centrifugal pump 230 propels the blood and preservation fluid via pump outlet line 234 into the integrated heat exchanger 210 which warms or cools the preservation fluid to a predetermined temperature. While it is preferred that donor organ 12 be maintained at a normothermic temperature of approximately 37° C., integrated heat exchanger 210 can also be used to lower the temperature of the preservation fluid down to a temperature of approximately 20° C. This heating and cooling function is performed by a water heater/cooler unit 236 which circulates temperature controlled water through the water side 238 of heat exchanger 210 via water circuit lines 240. The preservation fluid circulates through the second fluid side 242 of integrated heat exchanger 210 where it achieves the desired temperature.

The temperature controlled preservation fluid then flows through connecting line 244 and into the integrated membrane oxygenator 208. As part of this embodiment, the blood within the preservation fluid is oxygenated using a preferred mixture of 95%–97%$O_2$ and 3%–5% $CO_2$ at a rate of 1–5 L/min by membrane oxygenator 208. This mixture is provided to oxygenator 208 via input/output lines 246. As set forth above, the preferred oxygenator is a hollow fiber oxygenator, such as the Monolyth oxygenator manufactured by Sorin Biomedical or the MINIMAX PLUS manufactured by Medtronic. While not specifically shown in FIG. 5, membrane oxygenator 208 is provided with the requisite oxygen and carbon dioxide mixture from a regulated oxygen bottle 178 (FIG. 4). The oxygenator 208 further includes a plurality of outlets which allow the pressurized preservation fluid to be directed to other devices. It should be understood that at least one of the outlets from oxygenator 208 includes an integrated temperature monitoring probe (not shown) which can be used for monitoring the temperature of the fluid media exiting the oxygenator. More specifically, first outlet line 248 provides preservation fluid to an arterial filter 252. Preferably, filter 252 is a twenty (20) micron arterial filter, such as the pediatrics arterial filter manufactured by Medtronic. A second outlet line 250 serves as a recirculation line and provides preservation fluid to a leukocyte filter 254. Preferably, filter 254 is a micron leukocyte filter, such as the Pall leukocyte depleting filter manufactured by Pall Filters. Accordingly, filters 252 and 254 comprise the filtering means for removing the unwanted filtrate from the fluid media.

The output of arterial filter 252 is connected to a selector valve 50 via filter output line 48. Selector valve 50 is a multi-position stopcock which may be placed in one of several positions for directing fluid flow to either the initial perfusion line 52 (for antegrade perfusion via the aorta), the left atrium supply line 54 (for antegrade perfusion via the left atrium), or both lines simultaneously (for priming purposes). Additionally, selector valve 50 may be turned off completely. As previously discussed, lines 48, 54, and at times lines 52 and 58 form the arterial side 16 or delivery means of preservation circuit 202. The terminal end of the initial perfusion line 52 is connected into a tee or Y connector 56 which then branches to aorta line 58 and the afterload column, line 60. One end of tee 56 also includes a pressure transducer 256 which allows the pressure of the preservation fluid and more specifically the aortic root pressure to be monitored by a central signal processor and controller 560. A straight connector 258 is provided for connecting the adjustable height afterload column line 60 with the aorta return line 62. A luer port 63 having an anti-siphon valve secured to a stopcock thereon is integrated with connector 258 which acts as a one-way valve for allowing fluid pumped across connector 258 to flow through aorta return line 62 without syphoning additional fluid from afterload line 60.

The distal end of the afterload line 60 is attached to one of the connectors on a three-way port 260 for returning the preservation fluid to reservoir 212. As discussed above, aorta line 58 provides bi-directional flow to and from donor heart 12, depending upon which mode the preservation system 200 is operating. Additionally, the height of afterload column 60 is adjustable between a range of vertical positions for selectively changing the afterload pressure against which the donor heart 12 will beat or pump. It is contemplated that the height of afterload column 60 is adjusted by a feedback controlled electromechanical device in response to the coronary flow and aortic and/or left ventricle pressure signals received by controller 560. Once the preservation fluid pumped through afterload column 60 crosse stopcock connector 258 and anti-siphon luer port 63, it is returned to fluid reservoir 212 via aorta return line 62 by gravity. Additionally, a right ventricle return line 64 is connected between three-way port 260 and the cannula 122 of the pulmonary artery 132 for returning coronary effluent to fluid reservoir 212. Accordingly, lines 58, 60, 62 and 64 form the venous side 18 of preservation circuit 202 as they provide means for carrying fluid media away from the heart.

The aortic flow is measured by an ultrasonic flow probe 66 which is part of aorta line 58. Likewise, an ultrasonic flow probe 68 measures the coronary blood flow through right ventricle return line 64 of coronary effluent from the right ventricle to the fluid reservoir 212. The signals produced by flow probes 66, 68 are provided to inputs 66A, 68A, respectively, on system controller 560. Alternatively, the aortic and coronary flow signals produced by ultrasonic flow probes 66 and 68 are received by a multi-channel data recorder/controller such as flowmeter 70 shown in FIG. 1 or flowmeter 562 shown in FIG. 11 having at least two channels which assists in monitoring the condition of the donor heart 12, and the overall performance of preservation system 200. As previously discussed, one preferred flowmeter is the two-channel flowmeter manufactured by Transonic Systems. However, it is contemplated with this embodiment that a central controller 560 receive the signals produced by the various transducers as feedback signals, thereby monitoring all relevant signals from one central station. Alternatively, the signals from pressure transducers 72 and 256 may be monitored by a multi-channel data recorder and displayed on a lap top computer 564. The preferred device is an integrated hardware/software system such as the MacLab® manufactured by ADInstruments, Inc. These feedback signals can then be used for monitoring and controlling the pressure and flow provided by pump 230 via control line 580, as well as the temperature of heat exchanger 210 via bi-directional control line 582. Also shown is that central processor or controller 560 receives a temperature feedback signal 584 from the temperature probe output (not shown) of oxygenator 208.

The coronary flow is maintained within acceptable physiologic ranges (300–500 ml/min) by adjusting the height of the afterload column 60 above the heart 12 and adjusting the flow rate generated by pump 230. The afterload pressure is maintained at approximately 70 mm of mercury, but may be adjusted as necessary. A micro-tip pressure catheter 72 is inserted into the left ventricle via the left atrium 134 for measuring the intracavitary pressures of donor heart 12. A preferred pressure catheter 72 is of the type manufactured by Millar Instruments. All pressure measurements generated by pressure catheter 72 are recorded and displayed using a digital pressure recording system 74 such as that manufactured by Maclab which also assists in monitoring the condition of the preserved organ 12. As disclosed, pressure recording system 74 is capable of recording and displaying multiple pressure measurements. Alternatively, the signal generated by pressure catheter 72 may be received by central controller 560 on line for storage or display 72A.

As part of the present invention, it is contemplated that controller 560 also operate a mechanical actuator or arm 566 (FIG. 11) which is capable of automatically adjusting the height of afterload column 60 during the preservation period. This can be achieved through monitoring the flow signals produced by flow probe 66, 68 and the pressure signals produced by pressure transducer 256 and pressure catheter 72 which as shown are received by controller 560 on lines 256A and 72A, respectively.

Optionally, a pacemaker and internal defibrillator 220 may be connected to the ventricular walls of the preserved heart 12 via pacing leads 221 to correct by DC shock any unexpected arrhythmias during the preservation period.

A second port from oxygenator 208 provides outlet line 250 with oxygenated blood which is carried to leukocyte filter 254. Outlet line 262 from filter 254 delivers the preservation fluid to a hemodialysis filter 264 which is positioned in series with line 262 between a first stopcock 266 and a second stopcock 268. Hemodialysis filter 264 serves to remove metabolic waste products which may be produced by the preserved organ. The preferred hemodialysis filter 264 for this application is that manufactured by Cobe or Baxter.

The outlet from stopcock 268 provides the filtered blood to a two-port drip manifold 270 which receives the first and second preservation solutions from solution bags 272 and 274, respectively. As shown, drip manifold 270 includes two stopcock valves which assist in controlling the delivery of the chemical solutions of the present invention to the preservation fluid flowing through drip manifold 270. The outlet line 276 of drip manifold 270 is connected to three-way port 260 for delivering the enhanced preservation fluid back into fluid reservoir 212. While not specifically shown, it should be understood that an infusion pump is inserted between each solution bag 272, 274 and drip manifold 270 for individually controlling and regulating the drip rate of the chemical solutions contained in drip bags 272, 274 into drip manifold 270 as is well known in the art.

A variety of materials may be used for creating the various lines and components of preservation system 200. As almost all of the lines and components of preservation circuit 202 are in constant contact with the preservation fluid media, it is desirable to suppress the acute inflammatory response caused by exposure of the blood within the fluid to extracorporeal artificial surfaces. To alleviate this problem, all of the contact surfaces within perfusion circuit 14 may be coated or bonded with heparin to reduce complement and granulocyte activation. As an alternative, heparin may be directly introduced into the fluid media circulating through preservation circuit 202, or other bio-compatible surfaces may be utilized in circuit 202. The introduction of heparin assists in minimizing blood clotting within the circuit.

With continued reference to FIG. 5, the operation of preservation system 200 will be described in more significant detail. As described above, the donor heart is harvested in either the beating-state or the non-beating or arrested state and placed into preservation container 206. At this point, centrifugal pump 230 is propelling oxygenated and rewarmed blood through line 248. During priming, selector valve 50 is placed into the position which allows blood to flow simultaneously through the initial perfusion line 52 and the left atrium supply line 54. Once the arterial lines 16 of preservation circuit 202 are sufficiently primed to remove the presence of any air bubbles or air pockets, valve 50 is rotated into the position for supplying initial perfusion line 52 with fluid. Aortic line 58 can then be connected and secured to the aorta 130 using aortic cannula 120. This procedure allows blood to flow to the aortic line 58 for immediate perfusion of donor heart 12 via the aorta 130 in the non-working beating state.

Optionally, the stopcock on connector 258 may be closed for maximizing blood flow into the aorta 130. This procedure of antegrade perfusion via the aorta 130 is performed for approximately 10–15 minutes to allow for donor organ stabilization and to provide a period for instrumentation to be established. During this instrumentation period, the remaining flow lines are connected to donor heart 12. More specifically, the connection between aorta line 58 and the aorta 130 is completed and checked for leaks, supply line 54 is connected to the left atrium 134, and the right ventricle return line 64 is connected to the pulmonary artery 132. The pulmonary veins and superior and inferior vena cavae are then tied closed using surgical suture. During the initial connection protocol, any blood overflow is contained within preservation container 206 and returned to reservoir 212.

At the end of the stabilization period, the flow to the aorta 130 is reduced by rotating selector valve 50 to the normal operating position which simultaneously and gradually increases the flow to the left atrium 134 via left atrium supply line 54 and gradually shuts off flow through initial perfusion line 52. The stopcock of connector 258 is then opened which allows blood to flow through afterload line 60 and return line 62. This procedure then switches the donor heart 12 from the non-working state into the working state to ensure pulsatile coronary flow delivery, in which blood is pumped through the return lines 18 of preservation circuit 202 by the donor heart 12.

Blood flow to donor heart 12 through arterial or delivery lines 16 is assisted by centrifugal pump 230. The flow rate, pressure and temperature is monitored by controller 560 which adjusts the speed of pump head 230 for controlling the pressure and flow rate of the preservation fluid. The donor heart 12 is allowed to beat against an afterload pressure created by the vertical position of afterload column 60 above the preservation chamber 20 thereby generating a pulsatile coronary flow. Additionally, oxygenated blood is provided to the coronary vascular system, and de-oxygenated blood from the coronary vascular system is pumped from the right ventricle into the pulmonary artery return line 64 and returned to reservoir 212. At this point, donor heart 12 can be maintained in the viable beating state for the duration of the preservation period.

Figure 6:
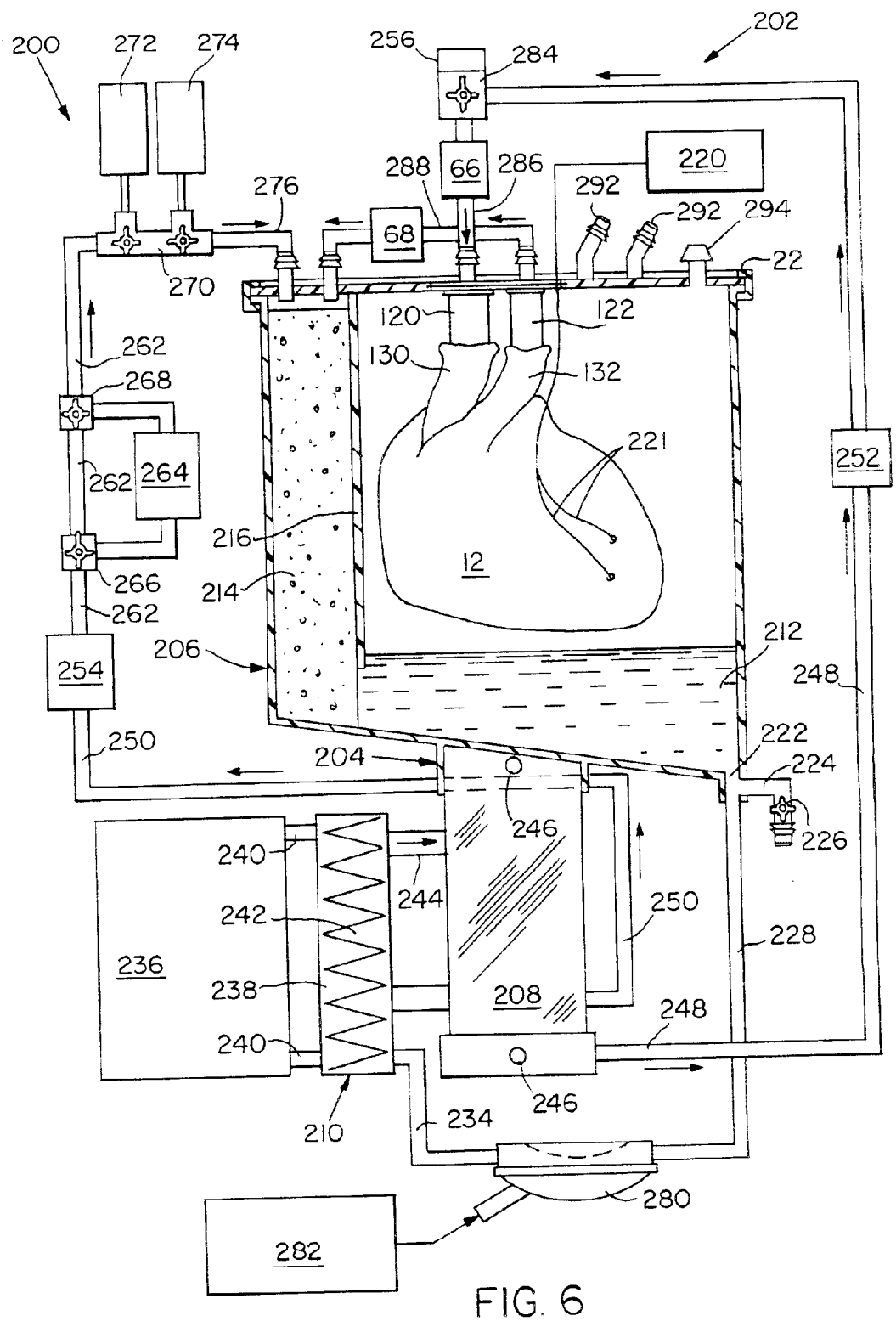
FIG. 6 is a schematic diagram of the preservation circuit in an alternate configuration and is shown utilizing a pulsatile pump for maintaining a heart in the non-working beating state according to an alternate embodiment of the present invention.

Turning now to FIG. 6, an alternate configuration of preservation system 200 is shown. As will be appreciated, the preservation system 200 illustrated in FIG. 6 comprises many of the components illustrated in FIG. 5. However, the primary distinguishing feature is that a pulsatile coronary flow is provided to donor heart 12 as opposed to a non-pulsatile or semi-constant flow. As such, this configuration allows several of the fluid carrying lines to be eliminated because the donor heart 12 is preserved in a beating non-working state.

In this embodiment, preservation system 200 includes a similar integrated preservation device 204 which includes the integrated preservation container 206 and reservoir 212, a hollow fiber membrane oxygenator 208, and an integrated heat exchanger 210. Oxygenator 208 and heat exchanger 210 are operated in substantially the same fashion as described above. As previously discussed, the preservation fluid stored within reservoir 212 flows through reservoir outlet 222 for delivery to a pulsatile pump 280 via outlet line 228. The pulsatile pump 280 is driven by a pulsed the electric control unit 282. The preferred pulsatile pump for this application is either the Heartmate electric assist pump manufactured by Thermo-Cardiosystems, Inc., or the Novacor® left ventricular assist pump manufactured by Baxter Healthcare Corporation. Alternatively, there are other pulsatile pumps, which are designed to less rigorous specifications which are also compatible with the preservation circuit 202 of this embodiment and which provide the function of pulsatile flow at a lower cost.

Accordingly, pulsatile pump 280 generates a pulsatile flow, as opposed to the constant flow produced by centrifugal pump 230. The flow of preservation fluid through seat exchanger 210 and oxygenator 208 is substantially similar to that described above. First outlet line 248 then carries the preservation fluid to arterial filter 252. The outlet of filter 252 is connected to a stopcock connector 284 having a similar pressure transducer 256 formed as an integral part thereof. The preservation fluid then flows through aorta delivery line 286 and into the aorta 130 via the aorta cannula 120. The pressure of the fluid in delivery line 286 can be monitored through pressure transducer 256. This method of delivering preservation fluid to the aorta 130 in the reverse direction allows the coronary vascular system to be perfused with the fluid media comprising oxygenated blood and the various chemical enhancers of the present invention. The coronary effluent is then pumped through the pulmonary artery 132 and into cannula 122. This coronary effluent is then carried through pulmonary artery return line 288 and back into fluid reservoir 212. It should be noted that re-circulation line 250 as well as the various components disposed there along, including leukocyte filter 254, hemodialysis filter 264 and drip manifold 270 operate in substantially the same manner as described above. Also shown is that aorta delivery line 286 and pulmonary artery return line 288 each include an ultrasonic flow probe 66, 68 (respectively) for measuring the flow rates through the delivery and return lines.

As part of the alternate configuration of FIG. 6, preservation container 206 is similarly sized for containing donor heart 12 and defies a fluid reservoir 212 for storing about 500–3000 ml of the fluid media. However, only one polyurethane filter 214 and one silicone defoaming screen 216 is utilized. As will be appreciated, this modification to preservation circuit 202 allows the use of only one line or delivery means for carrying oxygenated blood to the aorta 130, for supplying the coronary arteries using an antegrade perfusion technique, and one line or means connected to the pulmonary artery for carrying the coronary effluent (deoxygenated blood) away from the donor heart 12. Accordingly, there is no need for any additional cannulae or perfusion lines in communication with the left atrium due to the pulsatile flow provided by pulsatile pump 282. This pulsatile flow provides the physiologic characteristics of coronary flow for preventing coronary spasms, coronary endothelial damage, and for ensuring proper micro circulation for the preserved organ. By preserving donor heart 12 in the beating non-working state, a reduction in oxygen consumption and a reduction of stress of pumping against an afterload column can be achieved. This further results in a reduction in cellular metabolism and cellular waste, leading to a prolonged preservation period. Optionally, an intracardiac vent may be placed in the left ventricle to drain any blood that may leak through the aortic valve.

As part of the alternate configuration, preservation container 206 is similarly sized for containing donor heart 12 and defines a fluid reservoir 212 for storing about 500–3000 ml of the fluid media. However, an internal divider is present to separate the fluid media from the stored organ(not shown). In this configuration, the organ is placed in the top portion of the reservoir, separated from the fluid media of the circuit. This configuration allows for complete visualization of the preserved organ, during the preservation and transportation period.

While preservation of a donor heart which is intended for transplantation has been described above, it is within the scope of the present invention that preservation system 200 can also be used for maintaining a heart during reconstructive or other types of surgery. Accordingly, this procedure provides that an individual's heart can be removed and placed into the preservation circuit 202 of the present invention and operated upon outside of the body. In this scenario, the patient can be temporarily maintained with a suitable bypass and heart/lung machine as is well known in the art. However, removing the heart or any other organ for corrective surgery and maintaining the organ in a viable state allows procedures, which are normally considered complicated and high risk to be easily performed on the organ outside of the body. Once the surgery to the organ is complete, the organ is reimplanted into the original patient. Another application is removing and maintaining an organ and also perfusing the organ with chemotherapeutics for cancer treatment. Upon completion of the chemo procedure, the organ can be reimplanted. This technique would be especially useful for treating cancer of the liver, kidney or pancreas. Accordingly, the preservation system 200 according to the teachings of the present invention provides for a variety of applications in addition to maintaining a donor organ for transplantation in a viable state.

With reference now to FIGS. 7–10, alternate embodiments of the preservation system according to the teachings of the present invention are disclosed. Upon reviewing the following description, it will be appreciated that the preservation system of the present invention can also be utilized for preserving various solid organs including, but not limited to, the kidney, liver, lungs, pancreas, small intestine, and myocutaneous free flaps which can be used for transplantation to severe burn or trauma patients, or even cancer patients. The preservation system can also be used to maintain various vessels, such as the aorta, and vein grafts in a viable state for transplantation or plastic and reconstructive surgery. According to this aspect of the invention, the solid organ to be preserved or maintained in a viable state is contained within a soft shell bag which is specifically designed for the particular organ. At least one artery and one vein is cannulated so that the preservation fluid including compatible blood can be delivered to and carried away from the organ. Accordingly, the preservation circuit required for this alternate configuration is similar to that used for preserving a donor heart as described above.

Figure 7:
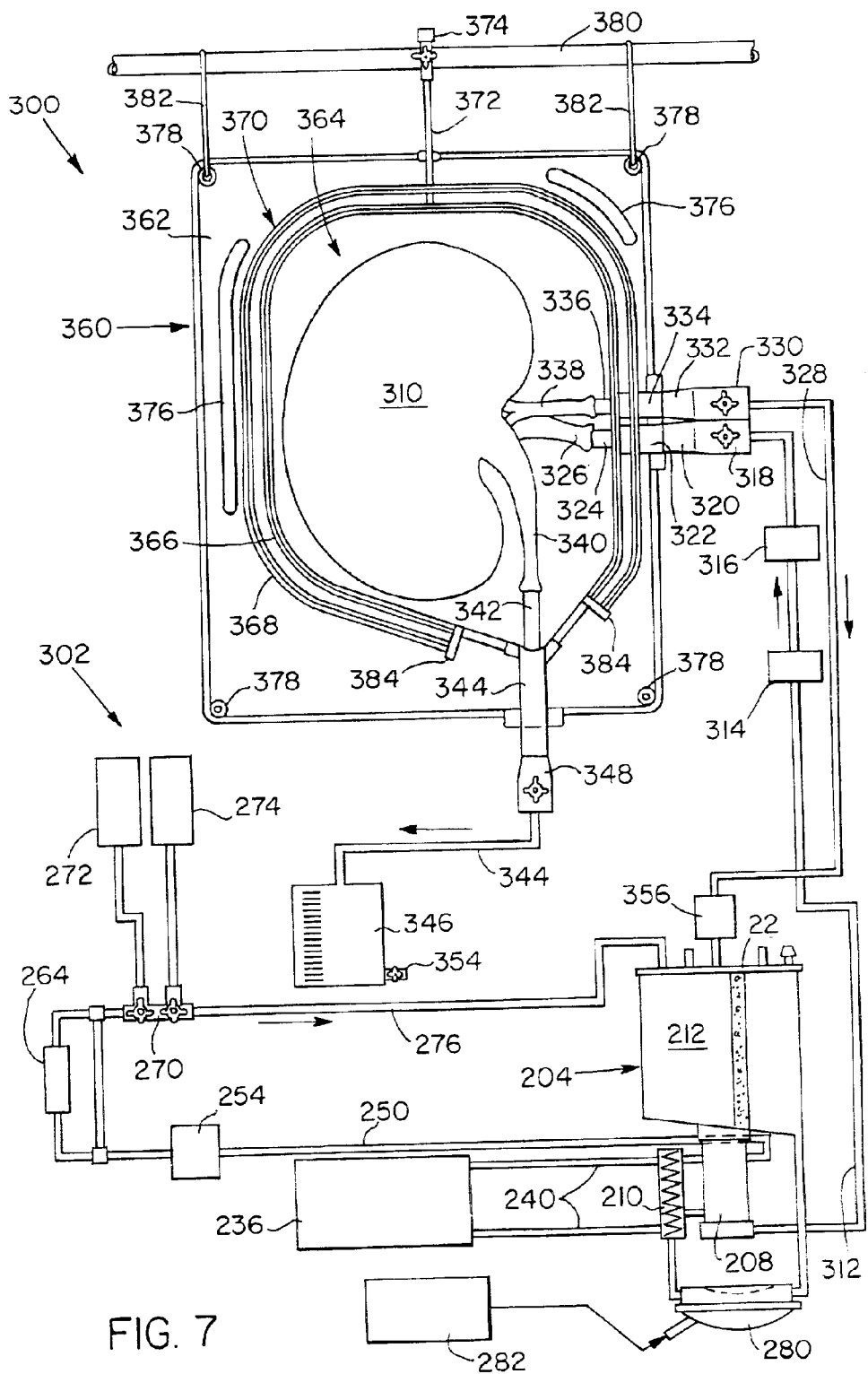
FIG. 7 is a schematic diagram of the preservation system and soft shell container for maintaining a kidney according to the teachings of the present invention.

With specific reference to FIG. 7, the preservation system 300 for preserving a kidney 310 is shown. The kidney preservation circuit 302 is operational for delivering oxygenated fluid to kidney 310 and carrying depleted fluid away from the kidney 310. Kidney preservation circuit 302 also utilizes an integrated preservation device 204 which defines a preservation container 206 and fluid reservoir 212, a heat exchanger 210, and an oxygenator 208. The warmed and oxygenated preservation fluid is carried from one port of oxygenator 208 to an arterial filter 314 via outlet line 312. An ultrasonic flow probe 316 measures the flow rate through line 312. Line 312 terminates at arterial stopcock connector 318. A pressure transducer 320 is formed at the opposite end of stopcock connector 318 and also connects to the arterial fitting 322 of the soft shell bag. An arterial cannula 324 is inserted within arterial fitting 322 and extends within the preservation chamber 364 of soft shell bag 360. Arterial cannula 324 then connects to the renal artery 326 for delivering the oxygenated preservation fluid to donor kidney 310. In a similar fashion, return line 328 extends between the top cover assembly 22 of fluid reservoir 212 and the venous stopcock connector 330. An ultrasonic flow probe 356 is also disposed along return line 328 for monitoring the returned flow of depleted fluid. The opposite end of connector 330 also includes a pressure transducer 332 which is used for monitoring the pressure of the depleted fluid media transported away from donor kidney 310. Pressure transducer 332 connects to venous fitting 334 which also includes a venous cannula 336 inserted therein. It is preferred that venous fitting 334 also be integrally formed with soft shell bag 360. Venous cannula 336 connects to the renal vein 338 of donor kidney 310. The ureter 340 of kidney 310 is connected to a ureter cannula 342 which is also integrated with a ureter connector 348 for carrying urine through line 344 and into graduated vessel 346. A stopcock connector 348 is provided along line 344 to allow the flow through line 344 to be halted in cases where vessel 346 must be changed, or where the urine must be sampled. Additionally, fluid may be released from vessel 346 through stopcock 354. The graduations on vessel 346 allow the urine production of kidney 310 to be monitored during the preservation period.

As with the other related embodiments, oxygenator 208 includes a second recirculation line 250 which delivers temperature controlled and oxygenated preservation fluid to a leukocyte filter 254 and an optional hemodialysis filter 264. The outlet of filter 264 connects to a similar two-port drip manifold 270 which receives the chemical solutions at various drip rates from solution bags 272, 274. The enhanced preservation fluid is returned to reservoir 212 via return line 276. The drip rates of the chemical solutions are controlled by a suitable infusion pump (not shown) as described above. As will be appreciated, either a centrifugal pump 230 or a pulsatile pump 280 can be used for circulating the fluid media through the circuit for preserving any of the solid organs.

The containment means associated with kidney preservation circuit 302 comprises a generally rectangular plastic bag 360 which includes a sealed body portion 362 and a preservation chamber 364. A defoaming material line the soft shell(not shown), an inner zip-lock closure 366 and an outer zip-lock closure 368 are situated at the outer perimeter of preservation chamber 364. Accordingly, these closures 366, 368 define a flap 370 which can be unzipped and opened with respect to the sealed body portion 362 for allowing the organ to be inserted and properly cannulated as described above. Closures 366, 368 are then sealed for containing the organ and defining the preservation chamber 364. Reinforcing members 384, which are formed by a heat seal, are located at the terminal ends of closures 366, 368. Two zip-lock closures 366, 368 are provided (as opposed to one) for enhanced structural rigidity, as well as for providing a primary seal and a secondary seal to prevent unwanted leaks of any residual fluid within preservation chamber 364. A vent assembly 372 is integrated within body portion 362 and extends below both zip-lock closures 366, 368 and into preservation chamber 364. The top of vent 372 includes a stopcock valve 374 which allows air to be extracted from or placed into preservation chamber 364. Additionally, it is contemplated that preservation chamber 364 could be filled with a bio-compatible fluid such as saline, or even a pharmaceutically active fluid through vent 372 after properly sealing flap 370.

Kidney preservation bag 360 may also be provided with one or more reinforcing ribs 376 which provide additional structural rigidity to the preservation bag and assist in maintaining a consistent shape. Additionally, a hole 378 is provided within each corner of preservation bag 360 which allows the bag to be suspended from a horizontal support member 380 by a pair of bag hangers 382. A particular advantage of the soft shell bag 360 is that ultrasound testing can be performed with kidney 310 remaining in bag 360 because the ultrasound probe can be placed against the organ while being protected by the bag.

Figure 8:
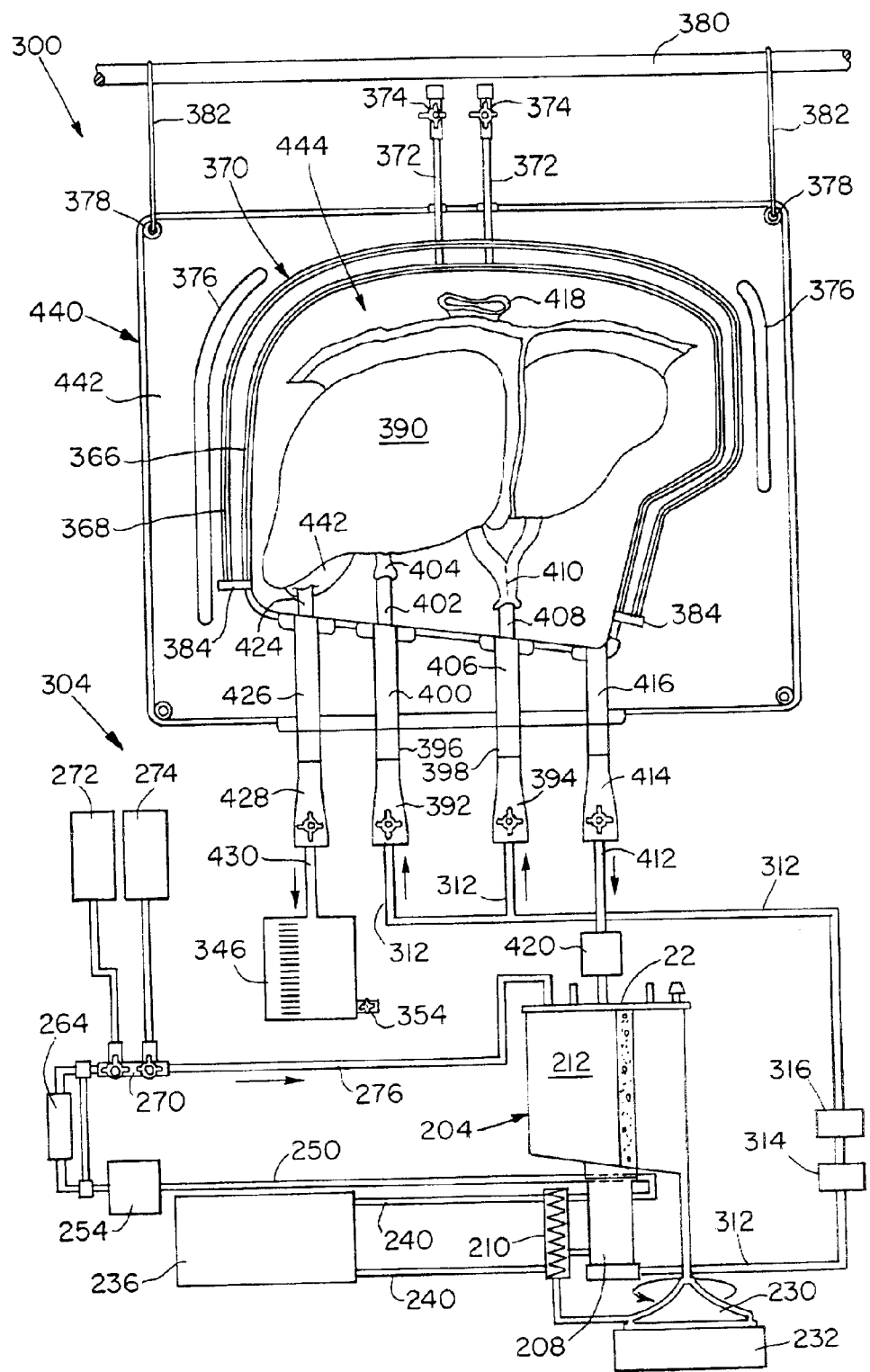
FIG. 8 is a schematic diagram of the preservation system and soft shell container for maintaining a liver according to the teachings of the present invention.

Turning now to FIG. 8, the preservation system 300 for preserving a liver is shown. The liver preservation circuit 304 is operational for delivering oxygenated fluid media to liver 390 and carrying depleted fluid away from the liver 390. Liver preservation circuit 304 also utilizes an integrated preservation device 204 which defines a preservation container 206 and fluid reservoir 212, a heat exchanger 210, and an oxygenator 208. The warmed and oxygenated preservation fluid is carried from one port of oxygenator 208 to an arterial filter 314 via outlet line 312. An ultrasonic flow probe 316 measures the flow rate through Line 312 as described above. At this point, line 312 branches into two lines, one terminating at arterial stopcock connector 392, and the other branch terminates at arterial stopcock connector 394. Each stopcock connector 392, 394 also includes a pressure transducer 396, 398 (respectively) formed at the opposite end thereof. Connector 392 also connects to arterial fitting 400 which is integrally formed with the soft shell bag. A suitable cannula 402 is inserted within arterial fitting 400 and extends within the preservation chamber 444 of soft shell liver bag 440. Cannula 402 then connects to the portal vein 404 for delivering the oxygenated preservation fluid to donor liver 390. The arterial stopcock connector 394 also connects to the arterial fitting 406 of the soft shell bag. An arterial cannula 408 is inserted within arterial fitting 406 and extends within the preservation chamber 444 of soft shell bag 440. Arterial cannula 408 then connects to the hepatic artery 410 which branches for delivering the oxygenated preservation fluid to right and left lobes of donor liver 390. In a similar fashion, a return line 412 extends between the top cover assembly 22 of fluid reservoir 212 and the return stopcock connector 414 which in turn connects to return fitting 416, also integrally formed within soft shell bag 440.

As shown, the inferior vena Cava 418 remains open and uncannulated so that the depleted preservation fluid can flow directly therefrom into preservation chamber 444. Accordingly, return fitting 416 provides an outlet for the depleted fluid to flow from and into return line 412. An ultrasonic flow probe 420 is disposed along return line 412 for monitoring the returned flow of depleted fluid. The gallbladder 422, still attached to liver 390, is connected to a suitable gallbladder cannula 424 which is also inserted with fitting 426. Stopcock connector 428 is connected to fitting 426 for regulating the flow of bile through line 430 and into graduated vessel 346. Stopcock connector 428 also allows the flow through line 430 to be halted in cases where vessel 346 must be changed or for sampling bile. Additionally, fluid may be released from vessel 346 through stopcock 354. The graduations on vessel 346 allow the bile production of gallbladder 422 to be monitored during the preservation period.

As with the other related embodiments, oxygenator 208 includes a second recirculation line 250 which delivers temperature controlled and oxygenated preservation fluid to a leukocyte filter 254 and an optional hemodialysis filter 264. The outlet of filter 264 connects to a similar two-port drip manifold 270 which receives the chemical solutions at various drip rates from solution bags 272, 274. The enhanced preservation fluid is then returned to reservoir 212 via return line 276. The drip rates of the chemical solutions are controlled by a suitable infusion pump (not shown) as described above.

The containment means associated with liver preservation circuit 304 also comprises a generally rectangular plastic bag 440 which includes a sealed body portion 442 and a preservation chamber 444. It should be noted that liver bag 440 shares many of the same components with kidney bag 360, which are described below.

An inner zip-lock closure 366 and an outer zip-lock closure 368 are situated at the outer perimeter of preservation chamber 444. Accordingly, these closures 366, 368 define a flap 370 which can be unzipped and opened with respect to the sealed body portion 362 for allowing the organ to be inserted and properly cannulated as described above. Closures 366, 368 are then sealed for containing the organ and defining the preservation chamber 364. Reinforcing members 384, which are formed by a heat seal, are located at the terminal ends of closures 366, 368. Two zip-lock closures 366, 368 are provided (as opposed to one) for enhanced structural rigidity, as well as for providing a primary seal and a secondary seal to prevent unwanted leaks of any residual fluid within preservation chamber 364. A pair of vent assemblies 372 are integrated within body portion 362 and extend below both zip-lock closures 366, 368 and into preservation chamber 444. The top of each vent 372 includes a stopcock valve 374 which allows air to be extracted from or placed into preservation chamber 444. Additionally, it is contemplated that preservation chamber 444 could be filled with a bio-compatible or even a pharmaceutically active fluid through vent 372 after properly sealing flap 370.

Liver preservation bag 440 may also be provided with one or more reinforcing ribs 376 which provide additional structural rigidity to the preservation bag and assist in maintaining a consistent shape. Additionally, a hole 378 is provided within each corner of preservation bag 440 which allows the bag to be suspended from a horizontal support member 380 by a pair of bag hangers 382.

Figure 9:
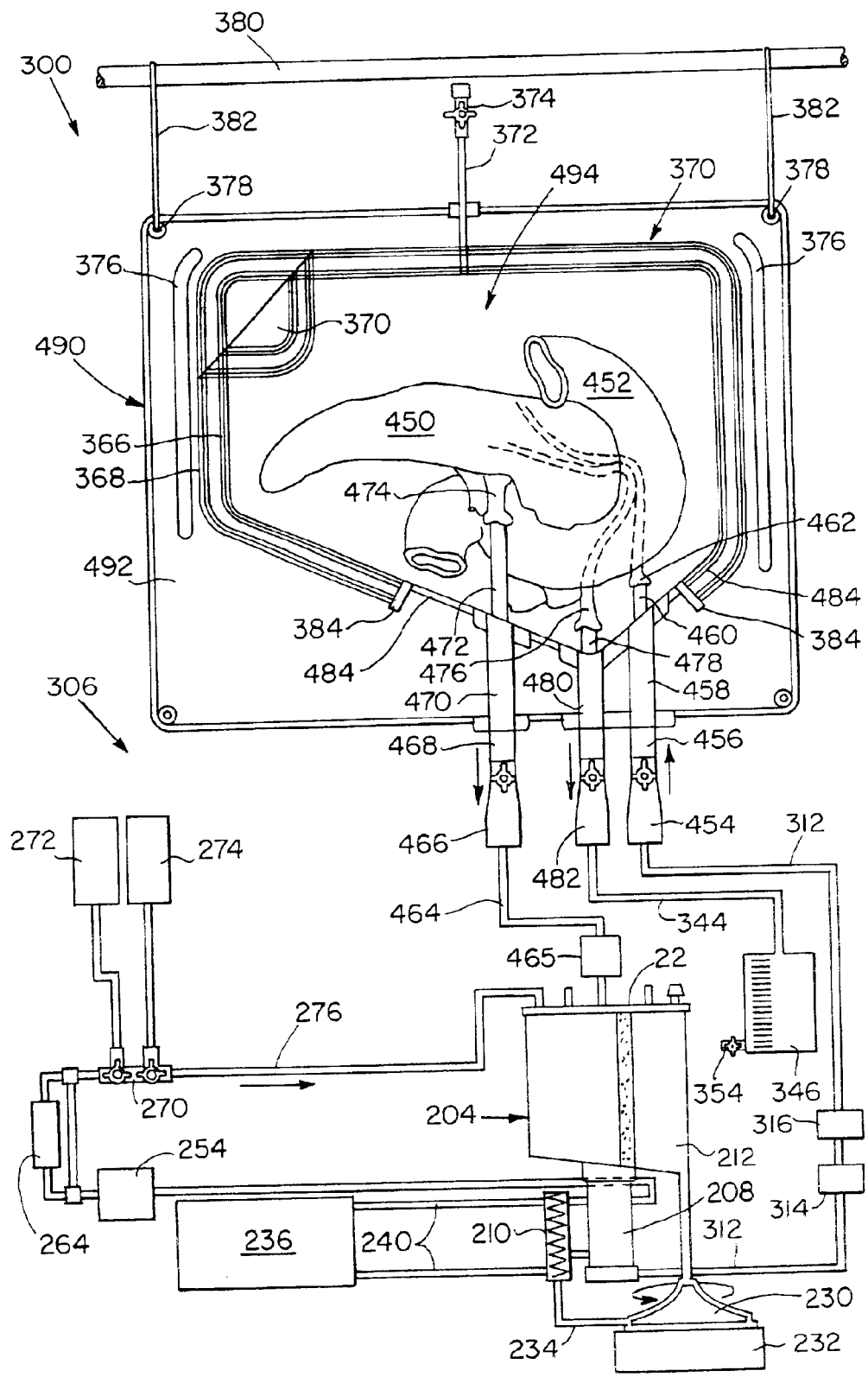
FIG. 9 is a schematic diagram of the preservation system and soft shell container for maintaining a pancreas according to the teachings of the present invention.

Turning now to FIG. 9, the preservation system 300 for preserving a pancreas 450 is shown, The pancreas preservation circuit 306 is also operational for delivering oxygenated fluid media to pancreas 450 and carrying depleted fluid away from the pancreas 450. As shown, the pancreas 450 is harvested along with the duodenum 452. Pancreas preservation circuit 306 also utilizes an integrated preservation device 204. The warmed and oxygenated fluid media is carried from one port of oxygenator 208 to an arterial filter 314 via outlet line 312. An ultrasonic flow probe 316 measures the flow rate through artery line 312. Line 312 terminates at arterial stopcock connector 454. A pressure transducer 456 is formed at the opposite end of stopcock connector 454 and also connects to the arterial fitting 458 which is integrally formed with the soft shell bag. An arterial cannula 460 is inserted within arterial fitting 458 and extends within the preservation chamber 494 of soft shell bag 490. Arterial cannula 460 then connects to the pancreatico/duodenal artery 462 for delivering the oxygenated preservation fluid to the pancreas 450. In a similar fashion, return line 464 extends between the top cover assembly 22 of fluid reservoir 212 and the venous stopcock connector 466. An ultrasonic flow probe 465 is disposed along return line 464. The opposite end of connector 466 also includes a pressure transducer 468 which is used for monitoring the pressure of the depleted fluid media transported away from pancreas 450. Pressure transducer 468 connects to venous fitting 470 which also includes a venous cannula 472 inserted therein. It is preferred that venous fitting 470 also be integrally formed within soft shell bag 490. Venous cannula 472 connects to the splenic and/or portal vein 474 of pancreas 450. The pancreatic duct 476 of pancreas 450 is connected to an appropriately sized cannula 478 which is also inserted within an integrated cannula fitting 480 for carrying pancreatic juices through line 344 and into a similar graduated vessel 346. A stopcock connector 482 is provided along line 344 as described above to allow the flow through line 344 to be halted in cases where vessel 346 must be changed. Additionally, fluid may be released from vessel 346 through stopcock 354. The graduations on vessel 346 allow the pancreatic juice production of pancreas 450 to be monitored during the preservation period.

As with the other related embodiments, oxygenator 208 includes a second recirculation line 250 which delivers temperature controlled and oxygenated fluid media to a leukocyte filter 254 and an optional hemodialysis filter 264. The outlet of filter 264 also connects to a two-port drip manifold 270 which receives the chemical solutions at various drip rates from solution bags 272, 274. The enhanced fluid media is returned to reservoir 212 via return line 276. The drip rate of the chemical solutions are similarly controlled by a suitable infusion pump (not shown) as described above.

The containment means associated with pancreas preservation circuit 306 comprises a generally rectangular plastic bag 490 which includes a sealed body portion 492 and a preservation chamber 494. An inner zip-lock closure 366 and an outer zip-lock closure 368 are situated at the outer perimeter of preservation chamber 494. Accordingly, these closures 366, 368 define a flap 370 which can be unzipped and opened with respect to the body portion 362 for allowing the organ to be inserted and properly cannulated as described above. As shown, one corner of flap 370 is unzipped to show its operation. Closures 366, 368 are then sealed for containing the organ and defining the preservation chamber 494. Reinforcing members 384, which are formed by a heat seal, are located at the terminal ends of closures 366, 368. Two zip-lock closures 366, 368 are provided (as opposed to one) for enhanced structural rigidity, as well as for providing a primary seal and a secondary seal to prevent unwanted leaks of any residual fluid within preservation chamber 494. A particular feature of pancreas bag 490 are the sloped portions 484 which serve to collect any residual fluid within the lowest portion of preservation chamber 494. A vent assembly 372 is integrated within body portion 492 and extends below both zip lock closures 366, 368 and into preservation chamber 494. The top vent 372 includes a stopcock valve 374 which allows air to be extracted from or placed into preservation chamber 494. Additionally, it is contemplated that preservation chamber 494 could be filled with a biocompatible fluid such as saline, or even a pharmaceutically active fluid (for contacting or bathing the exterior of the organ) through vent 372 after properly sealing flap 370. Pancreas preservation bag 490 may also be provided with one or more reinforcing ribs 376 which provide additional structural rigidity to the preservation bag (while being suspended) and further assist in maintaining a consistent shape. Additionally, a hole 378 is provided within each corner of preservation bag 490 which also allows the bag to be suspended from a horizontal support member 380 by a pair of bag hangers 382. A particular advantage of the soft shell bag 490 is that ultrasound testing can be performed on the organ preserved therein because the ultrasound probe can be placed against the organ while being protected by the plastic wall of the bag. It should be noted that the small intestine can be preserved in a similar fashion to the pancreas disclosed above.

Figure 10:
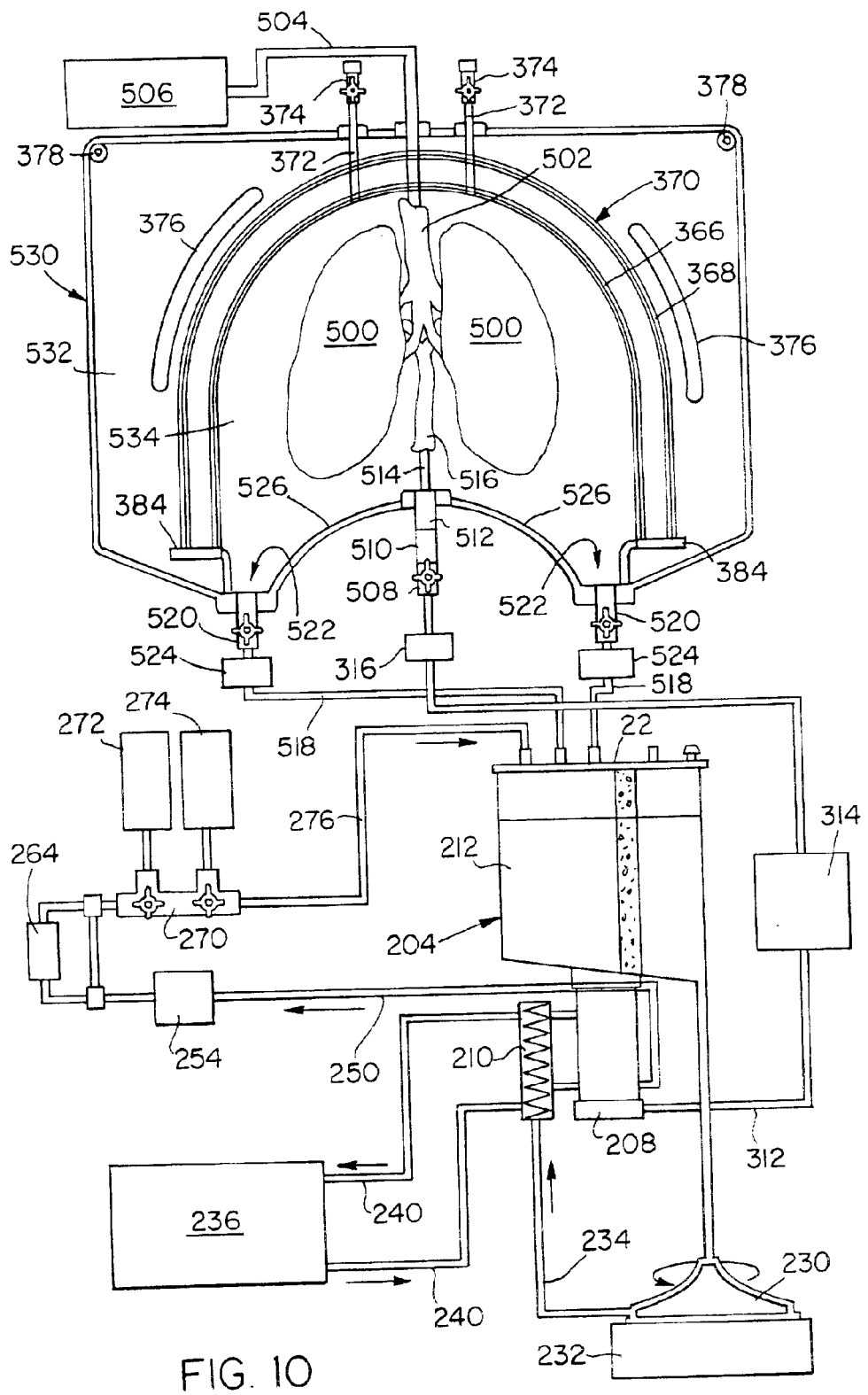
FIG. 10 is a schematic diagram of the preservation system and soft shell container for maintaining one or two lungs according to the teachings of the present invention.

With reference to FIG. 10, the preservation system 300 for preserving one or two lungs 500 is shown The lung preservation circuit 308 is also operational for delivering oxygenated fluid media to the lungs 500 and carrying depleted fluid away from the lungs 500. Lung preservation circuit 308 also utilizes an integrated preservation device 204 as shown and described above. The warmed and oxygenated preservation fluid media is carried from one port of oxygenator 208 to an arterial filter 314 via outlet line 312. An ultrasonic flow probe 316 measures the flow rate through line 312. Line 312 terminates at arterial stopcock connector 508. A pressure transducer S10 is formed at the opposite end of stopcock connector 508 and also connects to the arterial fitting 512 which is preferably molded or integrated with the soft shell bag. An arterial cannula 514 is inserted within arterial fitting 512 and extends within the preservation chamber 534 of soft shell bag 530. An arterial cannula 514 then connects to the pulmonary artery 516 which then branches to each lung for delivering the oxygenated preservation fluid media to the lungs 500. In a similar fashion as described above, a pair of return lines 518 extend between the top cover assembly 22 of fluid reservoir 212 and a pair of stopcock connectors 520. As shown, each stopcock connector 520 is integrally formed with soft shell bag 530, and is positioned in fluid communication with the collection portions 522 formed within preservation chamber 534. An ultrasonic flow probe 524 is disposed along each return line 518 for monitoring the returned flow of depleted fluid. While not specifically shown, the pulmonary veins of the lungs 500 are not cannulated, but rather are allowed to drain directly into the preservation chamber 534. As specifically shown, the lower portion of preservation chamber 534 includes an arcuate surface 526 for promoting flow of the depleted fluid into the collection portions 522.

As with the other related embodiments, oxygenator 208 includes a second recirculation line 250 which delivers temperature controlled and oxygenated preservation fluid to a leukocyte filter 254 and an optional hemodialysis filter 264. The outlet of filter 264 connects to a similar two-port drip manifold 270 which receives the chemical solutions at the predetermined drip rates from solution bags 272, 274. The 1 enhanced preservation fluid media is then returned to reservoir 212 via return line 276. The drip rates of the chemical solutions are also controlled by a suitable infusion pump (not shown) as described above.

The containment means associated with lung preservation circuit 308 also comprises a generally rectangular plastic bag 530 which includes a sealed body portion 532 and a preservation chamber 534. An inner zip-lock closure 366 and an outer zip-lock closure 368 are situated at the outer perimeter of preservation chamber 534. Accordingly, these closures 366, 368 also define a flap 370 which can be unzipped and opened with respect to the sealed body portion 532 for allowing the lungs to be inserted and properly cannulated as described above. Closures 366, 368 are then sealed for containing the lungs and defining the preservation chamber 534. Reinforcing members 384, which are formed by a heat seal, are located at the terminal ends of closures 366, 368. Two zip-lock closures 366, 368 are provided (as opposed to one) for enhanced structural rigidity, as well as for providing a primary seal and a secondary seal to prevent unwanted leaks of any residual fluid within preservation chamber 534. A pair of vent assemblies 372 are integrated within body portion 532 and extend below both zip-lock closures 366, 368 and into preservation chamber 534. The top of each vent 372 includes a stopcock valve 374 which allows bi-directional fluid communication with preservation chamber 534. As shown, the trachea 502 is connected to a ventilation tube and cannula 504 which is also integrally formed with lung preservation bag 530. A regulated volume of air is provided to ventilation line 504 by a suitable ventilation machine 506. As the lungs must be periodically ventilated by a suitable ventilation machine 506 to prevent collapse of the alveoli of the lung, this necessitates that the volume defined by preservation chamber 534 expand and contract to accommodate the corresponding expansion and contraction of lungs 500. Accordingly, opening vents 372 allows air movement in and out of preservation chamber 534. This expansion and contraction can be accomplished through any means for respirating the lungs.

Lung preservation bag 530 may also be provided with one or more reinforcing ribs 376 which function substantially as described above. Additionally, a hole 378 is provided within each corner-of preservation bag 530 which allows the bag to be suspended from a horizontal support member 380 by a pair of bag hangers 382. While this feature is not specifically shown, it should be understood that bag hangers 382 function as shown in FIGS. 7–9.

Figure 11:
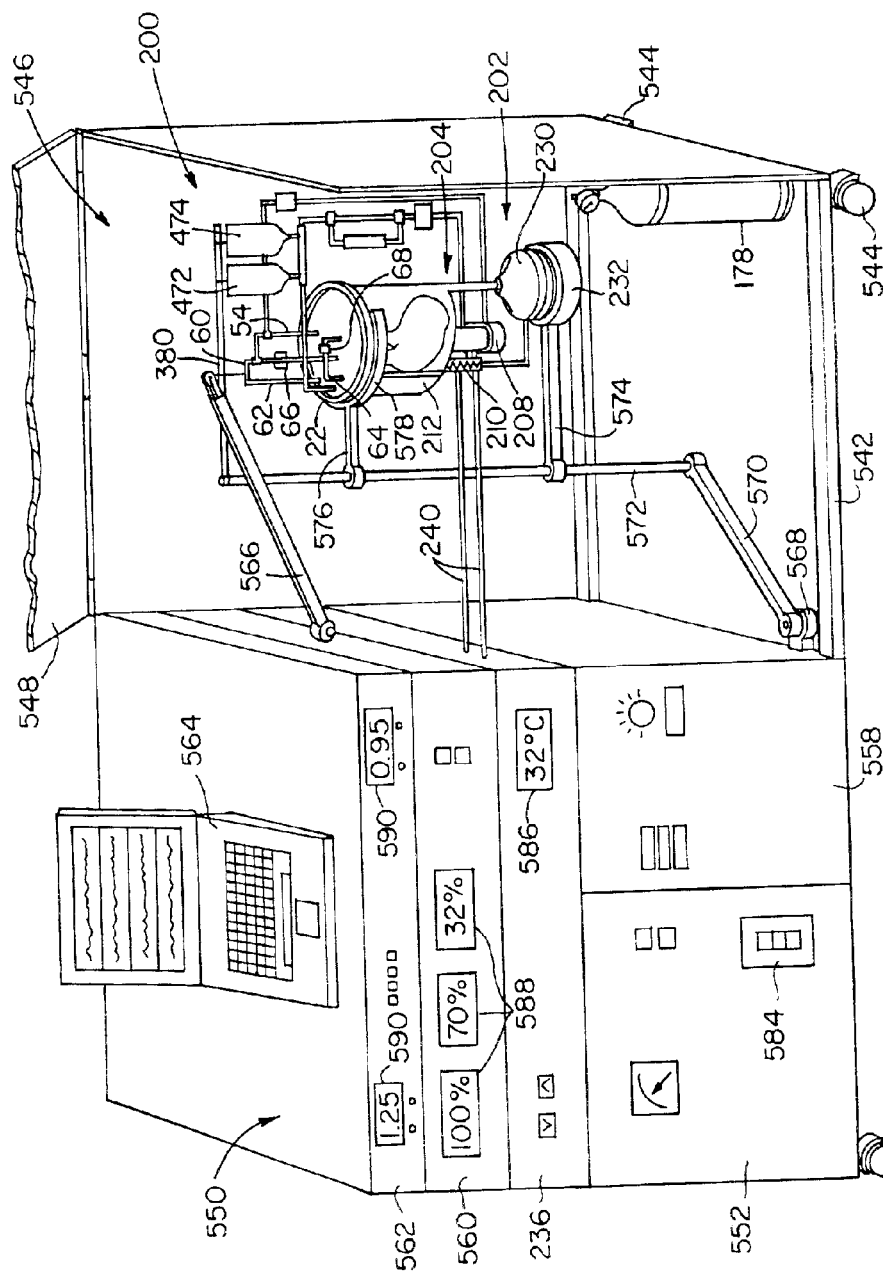
FIG. 11 is a perspective view of the portable preservation system for maintaining any number of organs according to the teachings of the present invention.

Turning now to FIG. 11, the portable preservation system 540 according to a preferred embodiment of the present invention is shown. More specifically, the portable preservation system 540 includes a body 542 having four locking casters 544. One side of portable preservation system 540 includes a storage area 546 for housing the components of preservation circuit 202. A cover 548 is provided for protecting preservation circuit 202 during transportation. The other side of portable preservation system 540 includes the electronics portion 550. As shown, electronics portion 550 includes a power source 552 having a battery and uninterruptable power supply (UPS) 554 and a power converter 556. As shown, the pump controller 558 is positioned next to power source 552, and can either be the controller for centrifugal pump 232 or the controller unit 282 for pulsatile pump 280. The heating/cooling control unit 236 is preferably disposed on top of power source 552 and pump controller 558. Also shown is that water circulation lines 240 extend between heat exchanger 210 and water heater/cooler unit 236. Additionally, a regulated oxygen tank 178 is secured within storage area 546. The system processor/controller 560 is disposed on top of water heater/cooler unit 236. Finally, the two-channel flowmeter 562 is integrated into the top of electronics portion 550. Also shown is a notebook style personal computer 564 which can be secured or integrated with the top of portable preservation system 540. The display of personal computer 564 is shown as displaying the various pressure and flow signals received from system controller 560. The system controller 560, also has a data logger (not shown) for digital storage of all data (flow, pressures, oxygen saturation, volume, and EKG activity) recorded during the preservation, transportation, evaluation, or resuscitation period.

The components within electronics portion 550 also include various displays for monitoring the operation of portable preservation system 540. More specifically, water heater/cooler unit 236 includes a temperature display 586. Central processor/controller 560 is shown to include three displays 588 for preferably displaying any of the data which is received and/or processed by central controller 560. Finally, flowmeter 562 is shown to include two displays 590 for presenting the flow rates of the preservation fluid media flowing through preservation circuit 202. Also shown is that mechanical control arm 566 is operated by and extends from system controller 560.

A particular feature of the portable preservation system 540 is the hinged arm 570, which is pivotably coupled to pivot bracket 568. A rod or pole 572 extends vertically from the outboard end of arm 570. Pole 572 can have various support brackets clamped thereto. More specifically, clamp bracket 574 supports pump driver 232. Clamp bracket 576 includes a semicircular member 578 for supporting integrated preservation container 204. Finally, a horizontal support member 380 is positioned so that solution bags 272 and 274 may be suspended therefrom.

It should be particularly noted that the portable preservation system 540 shown in FIG. 11 is not necessarily drawn to scale, and includes an exemplary preservation circuit 202 configured therein. Accordingly, it will be appreciated by the skilled artisan that any of the preservation circuits disclosed herein may be configured within storage area 546 and connected to electronics portion 550. While not specifically shown, it should be understood that the signals produced by pressure transducers 72, 256 and flow probes 66, 68 are connected into processor/controller 560 and flowmeter 562. It is also contemplated that controller 560 may also receive various signals from an integrated on-line hematocrite and oxygen saturation sensor, such as that manufactured by Medtronic. Additionally, the soft shell preservation bags 360, 440, 490, 530 for preserving or maintaining any solid organ may also be configured and suspended within storage area 546.

It is contemplated that the electrical components contained within portable presentation system 540 are powered by a specialized power source 552. As disclosed, power source 552 provides universal 110/220 VAC power at the appropriate 60/50 Hz level depending upon the electronic equipment contained therein. Power source 552 is also capable of receiving 110/220 VAC power at 60/50 Hz, as well as DC power ranging from 12 to 24 volts via receptacles. Thus, power source 552 also includes a bi-directional DC/AC power converter 556 which can accept power from a variety of sources which might be found in land based vehicles, ambulances and aircraft including airplanes and helicopters. It is further contemplated that power source 552 also includes some form of stored energy device in the form of UPS 554 for delivering the necessary level of power to the portable presentation system when external power is unavailable.

Figure 12:
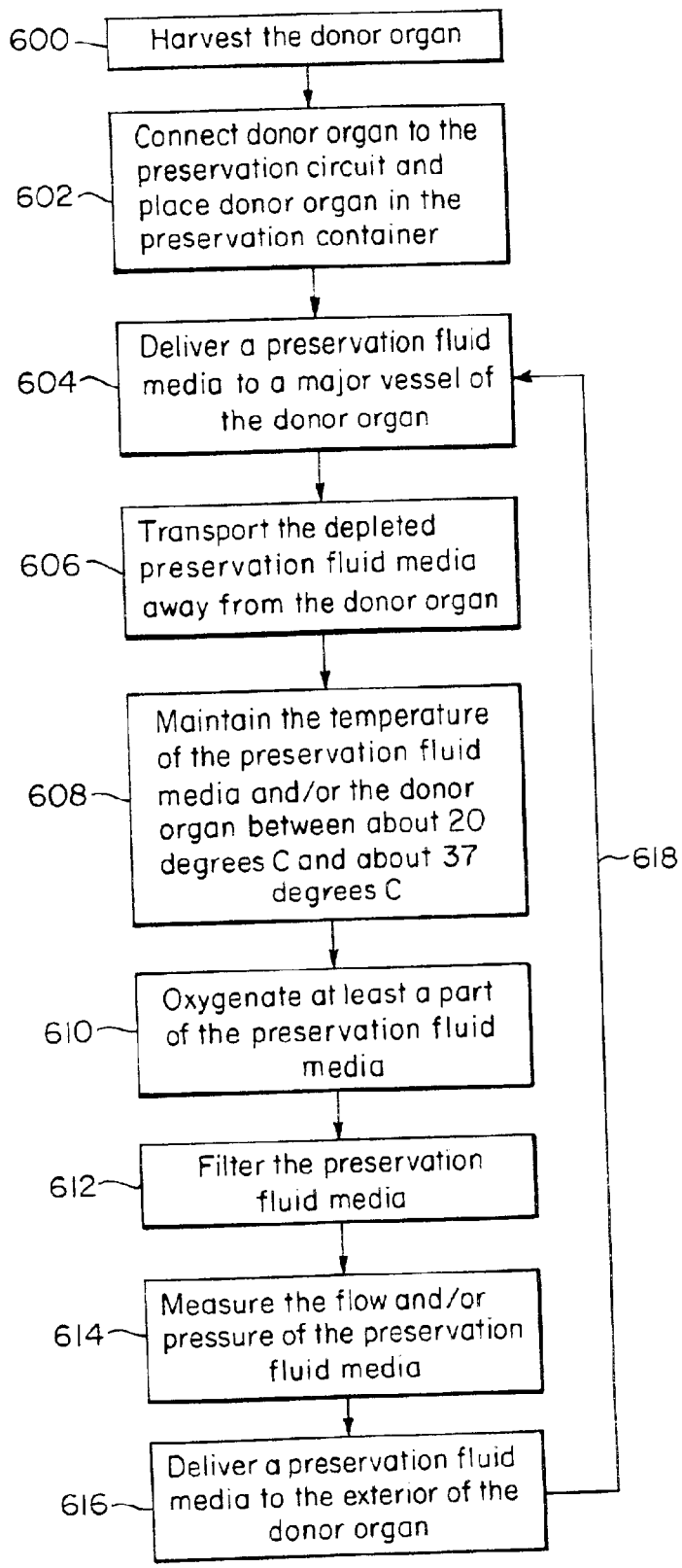
FIG. 12 is a flow diagram according to the method of the present invention.

Referring now to FIG. 12, the various methods associated with preservation systems 200 and 300 are summarized. Upon reviewing the following description, one skilled in the art will readily appreciate that the steps comprising the disclosed method are supported by the various exemplary embodiments of the present invention. In summary, the donor organ, such as donor heart 12 is harvested at block 600. Next, the donor organ is connected to the preservation circuit, such as preservation circuit 200, and also placed within the preservation container 206, as shown at block 602. At block 604, the preservation fluid media of the present invention is delivered to at least one major vessel, preferably an artery, of the donor organ. At block 606, the depleted preservation fluid media is transported away from the donor organ. At block 608, the temperature of the fluid media and/or the donor organ are maintained at a substantially normothermic temperature of between about 20° C. and about 37° C. At block 610, at least part of the preservation fluid media is oxygenated by oxygenator 208. At block 612, the preservation fluid media is filtered as described above. At block 614, the flow rate and/or pressure of the preservation fluid media can be measured and monitored, such as by central controller 560 and flowmeter 562. At block 616, the preservation fluid media can optionally be delivered to the exterior of the donor organ, for either bathing or providing the chemical solutions within the fluid media to the exterior of the organ. Finally, return line 618 represents that the preservation period can be continued for up to or exceeding twenty-four (24) hours by repeating the present method and continuing the delivery of preservation fluid to a major vessel of the donor organ at block 604.

The fluid media of the present invention comprises whole blood and a preservation solution. As noted above, certain of the compositions, methods and systems/devices of the present invention employ whole blood that is compatible with the organ(s) being preserved. Based upon experimental and clinical studies, it's been shown that donor or donor compatible blood perfusate is a more suitable alternative for clinical donor heart preservation because it provides better substrate, oxygen delivery, endogenous-free radical scavengers, potent buffers, and improved oncotic pressure. Whole blood that has had certain components or constituents removed that may have a deleterious effect in the organ(s) being preserved over time may optionally be employed. For example, in one embodiment, the whole blood is treated prior to being employed in the present invention by having been passed through a leukocyte depleting filter, resulting in leukocyte-depleted blood. It will be appreciated that, since one of the goals of the present invention is to provide an environment that most closely approximates the donor, the more compatible the whole blood, the better the overall chances of successful preservation.

The whole blood is mixed with a preservation solution in order to form a fluid composition (also referred to herein as fluid or fluid media). The fluid may be formed by mixing the whole blood with the elements of the preservation solution any time prior to delivery to the major vessel(s) selected and/or to the exterior of the organ such that the fluid or fluid media is provided to the vessels and also bathes or substantially surrounds the organ. The elements of the preservation solution can be admixed with the whole blood either singly or in any combination. For example, in one preferred embodiment, a shelf-stable preservation solution premix is formed by admixing a carbohydrate, sodium chloride, potassium, calcium, magnesium, bicarbonate ion, epinephrine and adenosine in advance of forming the fluid media. The final fluid media is then formed by combining the whole blood, the premix described above, as well as other desired fluid components which are not shelf-stable in such a premix such as insulin, just prior to delivery to the organ.

The fluids and/or the organ preservation solution of the present invention employ effective amounts of carbohydrates, electrolytes, hormones, and other pharmaceutically active or beneficial agents which are conventionally available for intra-venous or direct injection delivery. By the term "effective amount," as used herein, is meant an amount sufficient to provide a beneficial effect on the organ(s) being preserved. Without limitation, such beneficial effects include maintaining the organ's function, organ viability, implantability, transplantability, or an increase in or improvement of any of the foregoing over time. In one highly preferred embodiment, such effective amounts are employed such that the organ remains sufficiently viable for transplant 24 hours after removal from the donor, still more preferably 36 hours after removal; still more preferably 48 hours after removal; and yet more preferably, 72 hours after removal.

Examples of constituents which may be employed in the fluid media and/or preservation solution of the present invention include, without limitation: carbohydrates (glucose, dextrose); electrolytes (sodium, potassium, bicarbonates, calcium, magnesium); antibiotics and antimicrobials (gram negative and gram positive, e.g., penicillin at 250,000 to 1,000,000 units, preferably 250,000 units); hormones (insulin, epinephrin); endogenous metabolites or precursors of endogenous metabolites (adenosine, L-Arginine); fatty acids (saturated and unsaturated, short chain and long chain); and conventional pharmaceutically-active agents (such as heparin, nitroglycerin, ACE inhibitors, beta-blockers, calcium charnel blockers, cytoprotective agents, antioxidants, complements, anti-complements, immunosuppressive agents, nonsteroidal anti-inflammatories, anti-fungal medications, anti-viral medications, steroids, vitamins, enzymes, co-enzymes, and the like); and other materials conventionally employed for intravenous administration or direct injection to assist in delivery, bioavailability, or stability of the solution. Other constituents can also be used (as will be appreciated by the skilled artisan) that control pH, stabilize the solution, control viscosity, etc.

The following tables set forth in greater detail various constituents which may be used, either alone or in combination, in the fluids and/or organ preservation solution, at one or more of the stated levels. It should be noted that the levels given are the preferred levels, with the level indicated as P=as being at least one highly preferred level.

Because the present invention allows organs to be stored at normothermic conditions, and in a normal or near normal functioning state, the compositions and methods of the present invention are preferably substantially-free of agents used in hypothermic cold storage preservation solutions such as nonmetabilizable impermeants such as lactobionates, pentafraction, and the like.

In a preferred embodiment, the preservation solution and/or fluid media is maintained at a pH of about 7.35 to about 8.5; more preferably about 7.4 to about 7.6; and still more preferably about 7.4 to about 7.5.

TABLE 1

|  | Heart | Lung | Kidney | Liver | Pancreas |
| --- | --- | --- | --- | --- | --- |
| Carbohydrates | 2.5–5% | 2.5–5% | 2.5–5% | 2.5–5% | 2.5–5% |
| P = Dextrose | P = 5% | P = 5% | P = 5% | P = 5% | P = 2.5% |
| Sodium | 0.45–0.9% | 0.45–0.9% | 0.45–0.9% | 0.45–0.9% | 0.45–0.9% |
| Chloride (NaCL) | P = 0.9% | P = 0.9% | P = 0.9% | P = 0.9% | P = 0.9% |
| Potassium | 4–15 meq/L | 4–15 meq/L | 4–15 meq/L | 4–15 meq/L | 4–15 meq/L |
|  | P = 10 meq/L | P = 10 meq/L | P = 20 meq/L | P = 10 meq/L | P = 10 meq/L |
| Calcium | 0.25–1.5 gm/L | 0.25–1.5 gm/L | 0.25–1.5 gm/L | 0.25–1.5 gm/L | 0.25–1.5 gm/L |
|  | P = 0.5 gm/L | P = 0.5 gm/L | P = 0.5 gm/L | P = 0.5 gm/L | P = 0.5 gm/L |
| Antibiotics Antimicrobials+ | gram negative and/or gram positive coverage | gram negative and/or gram positive coverage | gram negative and/or gram positive coverage | gram negative and/or gram positive coverage | gram negative and/or gram positive coverage |
| Antifungals |  |  |  |  |  |
| 1. DiFlucan (Fluconazole) | 100–400 mg/L P = 100 mg/L | 100–400 mg/L P = 100 mg/L | 100–400 mg/L P = 100 mg/L | 100–400 mg/L P = 100 mg/L | 100–400 mg/L P = 100 mg/L |
| 2. Amphotericin B | 1–5 mg/L P = 1 mg/L | 1–5 mg/L P = 1 mg/L | 1–5 mg/L P = 1 mg/L | 1–5 mg/L P = 1 mg/L | 1–5 mg/L P = 1 mg/L |

TABLE 1-continued

|  | Heart | Lung | Kidney | Liver | Pancreas |
|---|---|---|---|---|---|
| Insulin | 20–60 U/L | 20–60 U/L | 20–60 U/L | 20–60 U/L | 20–60 U/L |
|  | P - 45 UL | P = 45 UL | P = 45 UL | P = 45 UL | P = 45 UL |
| Epinephrin | 0.5–4 mg/L | 0.5–4 mg/L | 0.5–4 mg/L | 0.5–4 mg/L | 0.5–4 mg/L |
|  | P = 1 mg/L | P = 0.5 mg/L | P = 1 mg/L | P = 1 mg/L | P = 1 mg/L |
| Magnesium | 0.5–2 mg/L | 0.5–2 mg/L | 0.5–2 mg/L | 0.5–2 mg/L | 0.5–2 mg/L |
|  | P = 1 gm/L | P = 1 gm/L | P = 1 gm/L | P = 1 gm/L | P = 1 gm/L |
| $NaHCO_3$ | 10–50 meq/L | 10–50 meq/L | 10–50 meq/L | 10–50 meq/L | 10–50 meq/L |
|  | P = 50 meq/L | P = 50 meq/L | P = 50 meq/L | P = 50 meq/L | P = 50 meq/L |
| Adenosine | 500 µmol/L–5 mmol/L | 500 µmol/L–5 mmol/L | 500 µmol/L–5 mmol/L | 500 µmol/L–5 mmol/L | 500 µmol/L–5 mmol/L |
|  | P = 2 mmoL | P = 2 mmoL | P = 2 mmoL | P = 2 mmoL | P = 2 mmoL |
| L-Arginine | 5 µmol/L–1 M/L | 5 µmol/L–1 M/L | 5 µmol/L–1 M/L | 5 µmol/L–1 M/L | 5 µmol/L–1 M/L |
|  | P = 0.5 m | P = 1 M | P = 0.5 M | P = 0.5 M | P = 0.5 M |
| SPM-5185 | 5–50 µmoL/L | 5–50 µmoL/L | 5–50 µmoL/L | 5–50 µmoL/L | 5–50 µmoL/L |
| Organic Nodoner | P = 10 µmoL | P = 20 µmoL | P = 10 µmoL | P = 10 µmoL | P = 10 µmoL |
| Heparin Sodium | 500–1500 U/L | 500–1500 U/L | 500–1500 U/L | 500–1500 U/L | 500–1500 U/L |
|  | P = 500 U/L | P = 500 U/L | P = 500 U/L | P = 500 U/L | P = 500 U/L |
| Nitroglycerin | 50–100 mg/L | 50–100 mg/L | 50–100 mg/L | 50–100 mg/L | 50–100 mg/L |
|  | P = 50 mg/L | P = 50 mg/L | P = 25 mg/L | P = 25 mg/L | P = 25 mg/L |
| ACE Inhibitors | 1–20 mg/L | 1–20 mg/L | 1–20 mg/L | 1–20 mg/L | 1–20 mg/L |
| Vasotec | P = 10 mg/L | P = 10 mg/L | P = 10 mg/L | P = 10 mg/L | P = 10 mg/L |
| Enalaprilat |  |  |  |  |  |
| Beta Blockers |  |  |  |  |  |
| 1. Lopressor | 100–450 mg/L | 100–450 mg/L | 100–450 mg/L | 100–450 mg/L | 100–450 mg/L |
| (Metoprolol Tartarate) | P = 200 mg/L | P = 200 mg/L | P = 200 mg/L | P = 200 mg/L | P = 200 mg/L |
| 2. Inderal | 10–100 mg/L | 10–100 mg/L | 10–100 mg/L | 10–100 mg/L | 10–100 mg/L |
| (Propanolol HCL) | P = 50 mg/L | P = 10 mg/L | P = 50 mg/L | P = 50 mg/L | P = 50 mg/L |
| $Ca^{++}$ Channel Blockers |  |  |  |  |  |
| 1. Cardizem (Diltiazem | 100–400 mg/L | 100–400 mg/L | 100–400 mg/L | 100–400 mg/L | 100–400 mg/L |
| HCL) | P = 350 mg/L | P = 350 mg/L | P = 350 mg/L | P = 350 mg/L | P = 350 mg/L |
| 2. Cardene | 30–150 mg/L | 30–150 mg/L | 30–150 mg/L | 30–150 mg/L | 30–150 mg/L |
| (Nicardipine) | P = 30 mg/L | P = 30 mg/L | P = 30 mg/L | P = 30 mg/L | P = 30 mg/L |
| Prostaglandin $E_1$ | 10–300 µg/L | 10–300 µg/L | 10–300 µg/L | 10–300 µg/L | 10–300 µg/L |
|  | P = 200 µg/L | P = 300 µg/L | P = 100 µg/L | P = 100 µg/L | NS |
| Lazaroids | 100–500 mg/L | 100–500 mg/L | 100–500 mg/L | 100–500 mg/L | 100–500 mg/L |
| (Antioxidants) | P = 300 mg/L | P = 300 mg/L | P = 300 mg/L | P = 300 mg/L | P = 300 mg/L |
| Complement |  |  |  |  |  |
| Neutralizers |  |  |  |  |  |
| 1. $SCR_1$ | As a priming solution | As a priming | As a priming | As a priming | As a priming |
| Soluble Complement | not drip | solution not drip | solution not drip | solution not drip | solution not drip |
| Receptor Type 1 | 100–1000 mg/L | 100–1000 mg/L | 100–1000 mg/L | 100–1000 mg/L | 100–1000 mg/L |
| Antibodies | P = 250 mg/L | P = 250 mg/L | P = 250 mg/L | P = 250 mg/L | P = 250 mg/L |
|  | priming fluid or | priming fluid or | priming fluid or | priming fluid or | priming fluid or |
|  | effective dose | effective dose | effective dose | effective dose | effective dose |
| 2. AntiComplement | 10–100 mg/L | 10–100 mg/L | 10–100 mg/L | 10–100 mg/L | 10–100 mg/L |
| Antibodies to C5a, | P = 50 mg/L | P = 50 mg/L | P = 50 mg/L | P = 50 mg/L | P = 50 mg/L |
| C5–9, CD 18 | effective dose | effective dose | effective dose | effective dose | effective dose |
| Prostacycline |  |  |  |  |  |
| Sdumedral* | As a priming solution | As a priming | As a priming | As a priming | As a priming |
| Methylprednisolone | not drip | solution not drip | solution not drip | solution not drip | solution not drip |
|  | 125–500 mg/L | 125–500 mg/L | 125–500 mg/L | 125–500 mg/L | 125–500 mg/L |
|  | P = 125 mg/L | P = 125 mg/L | P = 125 mg/L | P = 125 mg/L | P = 125 mg/L |
| Mannitol* | As a priming solution | As a priming | As a priming | As a priming | As a priming |
|  | not drip | solution not drip | solution not drip | solution not drip | solution not drip |
|  | 12.5–50 g/L | 12.5–50 g/L | 12.5–50 g/L | 12.5–50 g/L | 12.5–50 g/L |
|  | P = 12.5 g/L | P = 12.5 g/L | P = 12.5 g/L | P = 12.5 g/L | P = 12.5 g/L |

+See Tables 2A and 2B
*Priming solution means that the solution is brought to these levels and is not continuously added; it is simply replenished if there is additional transfusing.

TABLE 2A

| | | Antimicrobials | | | |
|---|---|---|---|---|---|
|  | Heart | Lung | Kidney | Liver | Pancreas |
| Flagyl | 500 mg/8 hrs Boluses | 500 mg/8 hrs | 500 mg/8 hrs | 500 mg/8 hrs | 500 mg/8 hrs |
| (Metronidazole) | or | Boluses or | Boluses or | Boluses or | Boluses or |
|  | 500–1000 mg/L | 500–1000 mg/L | 500–1000 mg/L | 500–1000 mg/L | 500–1000 mg/L |
|  | P = 1000 mg/L or ED* | P = 1000 mg/L or ED | P = 1000 mg/L or ED | P = 1000 mg/L or ED | P = 1000 mg/L or ED |

TABLE 2A-continued

Antimicrobials

| | Heart | Lung | Kidney | Liver | Pancreas |
|---|---|---|---|---|---|
| Cleocin (Clindamycin) | 600–900 mg/8 hrs. 600–900 mg/L P = 900 mg/L or ED | 600–900 mg/8 hrs. 600–900 mg/L P = 900 mg/L or ED | 600–900 mg/8 hrs. 600–900 mg/L P = 900 mg/L or ED | 600–900 mg/8 hrs. 600–900 mg/L P = 900 mg/L or ED | 600–900 mg/8 hrs. 600–900 mg/L P = 900 mg/L or ED |
| Bactrim (Trimethoprim/ Sulfamethoxazole) | 15–20 mg/L Boluses or ED | 15–20 mg/L Boluses or ED | 15–20 mg/L Boluses or ED | 15–20 mg/L Boluses or ED | 15–20 mg/L Boluses or ED |
| Vancomycin | 500–1 gm/12 hrs P = 500 mg/L or ED | 500–1 gm/12 hrs P = 500 mg/L or ED | 500–1 gm/12 hrs P = 500 mg/L or ED | 500–1 gm/12 hrs P = 500 mg/L or ED | 500–1 gm/12 hrs P = 500 mg/L or ED |

D = effect dose

TABLE 2B

Antibiotics

| | Heart | Lung | Kidney | Liver | Pancreas |
|---|---|---|---|---|---|
| Aminoglycosides (Family) | | | | | |
| 1. Amlkacin | 15 mg/L Boluses or ED* | 15 mg/L Boluses or ED | 15 mg/L Boluses or ED | 15 mg/L Boluses or ED | 15 mg/L Boluses or ED |
| 2. Geutamicin | ED | ED | ED | ED | ED |
| 3. Kanamycin | ED | ED | ED | ED | ED |
| 4. Neomycin sulfate | ED | ED | ED | ED | ED |
| 5. Streptomycin | ED | ED | ED | ED | ED |
| 6. Tobramycin | ED | ED | ED | ED | ED |
| Carbapanems (Theinamycins) (Family) | | | | | |
| 1. Imipenem & Cilastatin (Primaxin) | ED | ED | ED | ED | ED |
| Cephalosporins: 1st, 2nd & 3rd generations (Family) | | | | | |
| 1. Cejamandole (Mandol) | 0.5–1 gm/6–8 hrs. Boluses P = 1 gm/L or ED | 0.5–1 gm/6–8 hrs. Boluses P = 1 gm/L or ED | 0.5–1 gm/6–8 hrs. Boluses P = 1 gm/L or ED | 0.5–1 gm/6–8 hrs. Boluses P = 1 gm/L or ED | 0.5–1 gm/6–8 hrs. Boluses P = 1 gm/L or ED |
| 2. Kefzol (Cefazolin) | 1–2 gm/L P = 1 gm/L or ED | 1–2 gm/L P = 1 or ED | 1–2 gm/L P = 1 or ED | 1–2 gm/L P = 1 or ED | 1–2 gm/L P = 1 or ED |
| 3. Cefobid (Cefoperazone) | 2–4 gm/L P = 2 gm/L or ED | 2–4 gm/L P = 2 gm/L or ED | 2–4 gm/L P = 2 gm/L or ED | 2–4 gm/L P = 2 gm/L or ED | 2–4 gm/L P = 2 gm/L or ED |
| 4. Claforan (Cefotaxime) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 5. Cefotetan (Cefotan) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 6. Cefoxitin (Mefoxin) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 7. Fortaz (Ceftazidime) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 8. Cefizox (Ceftizoxime) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 9. Ceftriaxone (Rocephin) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 10. Zinacef (Cefuroxime) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 11. Keflin (Cephalothin) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| 12. Cefadyl (Cephapirin) | 1–2 gm/L P = 1 gm/L or ED | 1–2 gm/L P = 1 gm/L or ED | 1–2 gm/L P = 1 gm/L or ED | 1–2 gm/L P = 1 gm/L or ED | 1–2 gm/L P = 1 gm/L or ED |
| Macrolides (Family) | | | | | |
| 1. Erythromycin Gluceptate | 1–4 gm/L P = 1 gm or ED | 1–4 gm/L P = 1 gm or ED | 1–4 gm/L P = 1 gm or ED | 1–4 gm/L P = 1 gm or ED | 1–4 gm/L P = 1 gm or ED |
| 2. Erythromycin lactobionate | 1–4 gm/L P = 1 gm or ED | 1–4 gm/L P = 1 gm or ED | 1–4 gm/L P = 1 gm or ED | 1–4 gm/L P = 1 gm or ED | 1–4 gm/L P = 1 gm or ED |

TABLE 2B-continued

| | | | Antibiotics | | |
|---|---|---|---|---|---|
| | Heart | Lung | Kidney | Liver | Pancreas |
| Monobactams (Family) | | | | | |
| 1. Azactam (Aztreonam) | 1–2 gm/8 hrs. P = 1 gm/L or ED | 1–2 gm/8 hrs. P = 1 gm/L or ED | 1–2 gm/8 hrs. P = 1 gm/L or ED | 1–2 gm/8 hrs. P = 1 gm/L or ED | 1–2 gm/8 hrs. P = 1 gm/L or ED |
| Penicillins (Family) | | | | | |
| 1. Unasyn (Ampicillin/Sulbactam) | 1.5–3 gm/6 hrs. P = 1.5 gm/L or ED | 1.5–3 gm/6 hrs. P = 1.5 gm/L or ED | 1.5–3 gm/6 hrs. P = 1.5 gm/L or ED | 1.5–3 gm/6 hrs. P = 1.5 gm/L or ED | 1.5–3 gm/6 hrs. P = 1.5 gm/L or ED |
| 2. Geopen (Carbenicillin disodium) | 5 gm/4 hrs. or ED | 5 gm/4 hrs. or ED | 5 gm/4 hrs. or ED | 5 gm/4 hrs. or ED | 5 gm/4 hrs. or ED |
| 3. Mezlin (Meziocillin) | ED | ED | ED | ED | ED |
| 4. Pipracillin | ED | ED | ED | ED | ED |
| 5. Zosyn | ED | ED | ED | ED | ED |
| 6. Ticarcillin | ED | ED | ED | ED | ED |
| 7. Timentin | ED | ED | ED | ED | ED |
| 8. penicillin G | ED | ED | ED | ED | ED |
| 9. Methicillin | ED | ED | ED | ED | ED |
| 10. Oxacillin | ED | ED | ED | ED | ED |
| Quinolones (Family) | | | | | |
| 1. Ciprofloxacin | 200–500 mg/12 hrs. 400 mg/L or ED | 200–500 mg/12 hrs. 400 mg/L or ED | 200–500 mg/12 hrs. 400 mg/L or ED | 200–500 mg/12 hrs. 400 mg/L or ED | 200–500 mg/12 hrs. 400 mg/L or ED |
| 2. Ofloxacin | 200–500 mg/12 hrs. 400 mg/L or ED | 200–500 mg/12 hrs. 400 mg/L or ED | 200–500 mg/12 hrs. 400 mg/L or ED | 200–500 mg/12 hrs. 400 mg/L or ED | 200–500 mg/12 hrs. 400 mg/L or ED |
| Tetracyclines (Family) | | | | | |
| 1. Doxycycline | ED | ED | ED | ED | ED |
| 2. Minocycline | ED | ED | ED | ED | ED |

D = effect dose

The compositions, methods, and systems/devices of the present invention are particularly useful in that they can preserve organs for significant time periods in a normal or near-normal function state. They can accomplish this at normothermic or substantially normothermic temperatures. As used herein, normothermic or substantially normothermic means a temperature range of preferably about 20° C. to about 37° C., and still more preferably about 25° C. to about 37° C. It should be noted that normothermic outside the transplant art typically means about 37° C.; however, since the organ storage art has typically employed hypothermic to mean less than 20° C., and more typically about 4° C., the skilled artisan will appreciate that normothermic or substantially normothermic as applied to an organ being prepared for transplant carries a slightly different meaning in some contexts.

In addition to the significant advantage of being able to preserve organs in excellent condition for significantly longer time periods, another significant advantage of the present invention is that, because the organ is capable of being stored in a functioning condition, the organ can be tested and assessed much more easily and completely prior to implantation. For example, the following tests can be performed on the preserved organ, to evaluate its viability and function prior to transplant:

Heart continuous EKG monitoring to assess heart rate, rhythm and the viability of the conductance system of the organ; echocardiogram to assess wall motion, valve competence, and myocardial function (ejection fraction EF, etc.); measurement of pressures, cardiac output and coronary flow; metabolic assessment by calculating oxygen delivery, oxygen consumption, and oxygen demand; measure of blood chemistry (electrolytes, etc.), creatinine phosphokinase (CPK), complete blood count (CBC); and, assessment of myocardial function in response to inotropic agents and metabolic enhancers.

Kidney continuous measurement of urine output of the kidney; measurement of urinary excretion of sodium as a functional assessment of the kidney; measurement of the urinary osmolarity, to assess the concentration function of the kidney; measurement of serum and urinary blood urea nitrogen (BUN) and creatinin3; ultrasound analysis, to assess the structural integrity of the kidney; metabolic assessment of the preserved organ by calculating oxygen delivery, oxygen consumption, and, oxygen demand; and, measurement of blood chemistry (electrolytes, etc.), complete blood count (CBC).

Liver continuous measurement of bile production (indication of liver cell viability); measurement of liver function blood test (LFTs) levels (AST, ALT, alkaline phosphates, albumin, bilirubin (direct and indirect)); measurement of fibrinogen blood level (indication of liver cell ability to produce clotting factors); ultrasound analysis of the liver to assess liver parenchyma, intra- and extra-hepatic biliary tree; and, metabolic assessment of the liver by calculating oxygen delivery, oxygen consumption, and oxygen demand.

Pancreas: continuous measurement of pancreatic juice volume and chemical analysis; measurement of serum amylase and lipase levels to assess the viability of the pancreas; ultrasound analysis to assess structural architecture and pancreatic ducts integrity, diameter, and patience; measurement of serum insulin levels and glucose to assess the endocrine function of the pancreas; and, metabolic assessment of the pancreas by calculating oxygen delivery, oxygen consumption, and oxygen demand.

Small Intestine: visual inspection of peristaltic movement of the bowel, indicating viable bowel muscle and nerve conduction; visual inspection of bowel color to assess bowel blood supply and viability; metabolic assessment by calculating oxygen delivery, oxygen consumption, and oxygen demand; and, measurement of blood chemistry (electrolytes, etc.) complete blood count (CBC).

By employing the compositions, methods and systems/devices of the present invention, the organ can also be removed and treated in the functioning state. For example, cytotoxic therapeutic agents such as antineoplastic agents or vectors could be delivered to the organ in an isolated fashion. In addition, other therapeutic protocols, appreciated by those skilled in the art, e.g., gene therapy, may be applied to the organ, prior to implantation. In addition, a harvested cadaveric organ may be resuscitated (usually within 10 to 60 minutes of death), and the viability of the organ analyzed, e.g., by the above-described methods.

While this invention has been particularly shown and described with references to preferred embodiments thereof, it will be understood by those skilled in the art that various changes in form and details may be made therein without departing from the scope of the invention encompassed by the appended claims.

What is claimed is:

1. An organ preservation solution for the preservation of a human or human-compatible harvested organ in a functioning state comprising:
    (1) a metabolizable carbohydrate at a concentration between 2.5% and 3%;
    (2) sodium chloride at a concentration between 0.45% and 0.9%;
    (3) potassium ion at a concentration between 4 meq/L and 10 meq/L;
    (4) calcium ion at a concentration between 0.25 gm/L and 1.5 g/L;
    (4) magnesium ion at a concentration between 0.5 gm/L and 0.7 gm/L;
    (6) bicarbonate ion at a concentration between 10 meq/L and 20 meq/L;
    (7) epinephrin at a concentration between 0.5 mg/L and 2 mg/L;
    (8) adenosine at a concentration between 500 $\mu$mol/L and 1 mmol/L; and
    (9) at least one fatty acid; wherein said solution is substantially free of non metabolizable impermeants; and further wherein said solution has a pH of about 7.4 to about 8.5.

2. A solution according to claim 1 wherein said solution further comprises a pharmaceutically active agent selected from the group consisting of heparin, nitroglycerin, an ACE inhibitor, a beta blocker, a calcium channel blocker, a cytoprotective agent, an antioxidant, an anti-fungal agent, an anti-viral agent, an anti-bacterial agent, an immunosuppressive agent, a nonsteroidal anti-inflammatory agent, a steroid, vitamins and mixtures thereof.

3. A solution according to claim 2 wherein said solution further includes insulin.

4. A solution according to claim 2 wherein said solution further includes a complement neutralizer.

5. A solution according to claim 2 wherein said metabolizable carbohydrate is glucose.

6. A method of preserving a human or human-compatible harvested organ in a functioning state during a preservation period prior to implantation comprising:
    (a) providing an organ in need of preservation;
    (b) providing containment means for said organ;
    (c) providing a preservation fluid media; said fluid media comprising:
        (i) whole blood or leukocyte-depleted whole blood that is compatible with said organ; and
        (ii) a preservation solution comprising:
        (a) a metabolizable carbohydrate;
        (b) sodium chloride;
        (c) potassium ion;
        (d) calcium ion;
        (e) magnesium ion;
        (f) bicarbonate; epinephrin; and adenosine;
    (d) delivering said fluid media to at least one major vessel of said contained functioning organ while said organ is maintained at a normothermic temperature of about 20° C. to about 37° C.

7. A method according to claim 6 wherein said media includes heparin.

8. A method according to claim 6 wherein said media further includes a pharmaceutically active agent selected from the group consisting of nitroglycerin, an ACE inhibitor, a beta blocker, a calcium channel blocker, a cytoprotective agent, an antioxidant, an anti-fungal agent, an anti-viral agent, an anti-bacterial agent, an immunosuppressive agent, a nonsteroidal anti-inflammatory agent, a steroid, and mixtures thereof.

9. A method according to claim 6 wherein said media further includes at least one fatty acid.

10. A method according to claim 9 wherein said method includes the further step of delivering said fluid media to the exterior of said organ.

11. A method according to claim 6 wherein said method includes the further step of filtering said fluid media as metabolic products from said organ accumulate in said fluid media.

12. A method according to claim 6 wherein said method includes the further step of oxygenation at least a part of said fluid media.

13. A method according to claim 6 wherein said method comprises the further step of measuring the flow of said fluid media.

14. A method according to claim 6 wherein said method comprises the further step of measuring the pressure of said fluid media.

15. A method according to claim 6 wherein the harvested organ is selected from the group consisting of heart, kidney, liver, lung, pancreas, small intestine, blood carrying vessel, and myocutaneous free flap.

16. A method according to claim 15 wherein the organ preserved is a heart.

17. A method of claim 6 wherein said media includes insulin.

* * * * *